US012577529B2

(12) United States Patent
Williams et al.

(10) Patent No.: US 12,577,529 B2
(45) Date of Patent: Mar. 17, 2026

(54) METHODS FOR PRODUCING NEURAL CELLS

(71) Applicant: QUIVER HOLDINGS INC., Cambridge, MA (US)

(72) Inventors: Luis Williams, Cambridge, MA (US); Vaibhav Joshi, Cambridge, MA (US); Graham T. Dempsey, Sudbury, MA (US)

(73) Assignee: QUIVER HOLDINGS INC., Cambridge, MA (US)

( * ) Notice: Subject to any disclaimer, the term of this patent is extended or adjusted under 35 U.S.C. 154(b) by 0 days.

(21) Appl. No.: 17/842,344

(22) Filed: Jun. 16, 2022

(65) Prior Publication Data

US 2022/0403331 A1      Dec. 22, 2022

Related U.S. Application Data

(60) Provisional application No. 63/211,693, filed on Jun. 17, 2021.

(51) Int. Cl.
| | |
|---|---|
| *C12N 5/079* | (2010.01) |
| *C12N 5/00* | (2006.01) |
| *C12N 5/0735* | (2010.01) |

(52) U.S. Cl.
CPC ......... *C12N 5/0618* (2013.01); *C12N 5/0068* (2013.01); *C12N 5/0606* (2013.01); *C12N 2501/60* (2013.01); *C12N 2502/086* (2013.01); *C12N 2506/02* (2013.01); *C12N 2506/1307* (2013.01); *C12N 2533/52* (2013.01)

(58) Field of Classification Search
CPC .. C12N 5/0618; C12N 5/0068; C12N 5/0606; C12N 2501/60; C12N 2502/086; C12N 2506/02; C12N 2506/1307; C12N 2533/52
See application file for complete search history.

(56) References Cited

U.S. PATENT DOCUMENTS

| | | |
|---|---|---|
| 5,789,538 A | 8/1998 | Rebar et al. |
| 5,925,923 A | 7/1999 | Blair |
| 6,007,988 A | 12/1999 | Choo et al. |
| 6,013,453 A | 1/2000 | Choo et al. |
| 6,140,466 A | 10/2000 | Barbas et al. |
| 6,200,759 B1 | 3/2001 | Dove et al. |
| 6,242,568 B1 | 6/2001 | Barbas et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,534,261 B1 | 3/2003 | Cox et al. |
| 6,607,882 B1 | 8/2003 | Cox et al. |
| 6,903,185 B2 | 6/2005 | Kim et al. |
| 7,153,949 B2 | 12/2006 | Kim et al. |
| 8,492,145 B2 | 7/2013 | Nakayama et al. |
| 10,613,079 B2 | 4/2020 | Eggan et al. |

| | | |
|---|---|---|
| 2005/0064474 A1 | 3/2005 | Urnov et al. |
| 2006/0188987 A1 | 8/2006 | Guschin et al. |
| 2008/0274446 A1 | 11/2008 | Stice et al. |
| 2016/0298080 A1 | 10/2016 | Ying et al. |
| 2020/0018746 A1 | 1/2020 | Tekin et al. |
| 2020/0056149 A1 | 2/2020 | Tomishima et al. |
| 2020/0191776 A1 * | 6/2020 | Eggan ................ G01N 33/6872 |

FOREIGN PATENT DOCUMENTS

| | | | |
|---|---|---|---|
| WO | 2018/165577 A1 | 9/2018 | |
| WO | WO-2021086063 A1 * | 5/2021 | ......... A61K 49/0008 |

OTHER PUBLICATIONS

Schmid, B., et al., "Generation of two gene edited iPSC-lines carrying a DOX-inducible NGN2 expression cassette with and without GFP in the AAVS1 locus," Stem Cell Research 52: 102240. doi: 10.1016/j.scr.2021.102240. Epub Feb. 11, 2021. (Year: 2021).*

Shih, P. Y., et al., "Development of a fully human assay combining NGN2-inducible neurons co-cultured with iPSC-derived astrocytes amenable for electrophysiological studies," Stem Cell Research 54: 102386. doi: 10.1016/j.scr.2021.102386. Epub May 24, 2021. (Year: 2021).*

Deneault, E., et al., "Complete Disruption of Autism-Susceptibility Genes by Gene Editing Predominantly Reduces Functional Connectivity of Isogenic Human Neurons," Stem Cell Reports 11(5): 1211-1225. doi: 10.1016/j.stemcr.2018.10.003. Epub Nov. 1, 2018. (Year: 2018).*

Sagal et al., "Proneural transcription factor Atoh1 drives highly efficient differentiation of human pluripotent stem cells into dopaminergic neurons," Stem Cells Translational Medicine 3: 888-898 (Year: 2014).*

Baker, N. E., and Brown, "All in the family: proneural bHLH genes and neuronal diversity," Development 145(9): dev159426. doi: 10.1242/dev.159426. (Year: 2018).*

Serra, M., et al., "Microencapsulation technology: a powerful tool for integrating expansion and cryopreservation of human embryonic stem cells," PLoS One 6(8): e23212. doi: 10.1371/journal.pone. 0023212. (Year: 2011).*

Hall, P.E., et al., "Laminin enhances the growth of human neural stem cells in defined culture media," BMC Neurosci 9: 71. doi: 10.1186/1471-2202-9-71. (Year: 2008).*

Bardy, C. et al., "Neuronal medium that supports basic synaptic functions and activity of human neurons in vitro," Proc Natl Acad Sci USA 112(20): E2725-E2734. doi: 10.1073/pnas.1504393112. (Year: 2015).*

Kampmann, M., "CRISPR-based functional genomics for neurological disease," Nat Rev Neurol 16(9):465-480. doi: 10.1038/s41582-020-0373-z. Epub Jul. 8, 2020. (Year: 2020).*

(Continued)

*Primary Examiner* — Tracy Vivlemore
*Assistant Examiner* — Eric J Rogers
(74) *Attorney, Agent, or Firm* — Thomas C. Meyers; Sullivan & Worcester LLP

(57) ABSTRACT

The present invention provides differentiated neural cells and methods for making differentiated neural cells from pluripotent stem cells (PSC) at an industrial scale sufficient for high-throughput assays. The methods of the invention allow billions of PSCs and/or neural cells differentiated from the PSCs to be cryopreserved and expanded at multiple steps.

10 Claims, 5 Drawing Sheets

(56) References Cited

OTHER PUBLICATIONS

Engle, S. J., et al., "Best Practices for Translational Disease Modeling Using Human iPSC-Derived Neurons," Neuron 100(4):783-797. doi: 10.1016/j.neuron.2018.10.033. (Year: 2018).*

Alami, et al., "Microtubule-dependent transport of TDP-43 mRNA granules in neurons is impaired by ALS•causing mutations", Neuron 81(3):536-543.

Almeida, et al., "Modeling key pathological features of frontotemporal dementia with C9ORF72 repeat expansion in iPSC-derived human neurons", Acta Neuropathol 126(3):385-399.

Amorso, et al., "Accelerated high-yield generation of limb-innervating motor neurons from human stem cells", J Neurosci 33(2):574-86.

An, et al., "Genetic correction of Huntington's disease phenotypes in induced pluripotent stem cells", Cell Stem Cell 11(2):253-263.

Ananiev, et al., "Isogenic pairs of wild type and mutant induced pluripotent stem cell (iPSC) lines from Rett syndrome patients as in vitro disease model", PLoS One 6(9):e25255.

Andrade, et al., "Evidence for premature aging due to oxidative stress in iPSCs from Cockayne syndrome", Hum Mol Genet 21:3825-3834 (2012).

Bardy, et al., "Neuronal medium that supports basic synaptic functions and activity of human neurons in vitro", Proc Natl Acad Sci USA 112:E2725-34 (2015).

Bilican, et al., "Mutant induced pluripotent stem cell lines recapitulate aspects of TDP-43 proteinopathies and reveal cell-specific vulnerability", PNAS 109(15):5803-5808.

Boulting, et al., "A functionally characterized test set of human induced pluripotent stem cells", Nat Biotech 29(3):279-286.

Brennand, et al., "Modelling schizophrenia using human induced pluripotent stem cells,", Nature 473 (7346):221-225.

Camnasio, et al., "The first reported generation of several induced pluripotent stem cell lines from homozygous and heterozygous Huntington's disease patients demonstrates mutation related enhanced lysosomal activity", Neurobiol Dis 46(1):41-51.

Chiang, et al., "Integration•free induced pluripotent stem cells derived from schizophrenia patients with a Disc 1 mutation", Molecular Psych 16:358-360.

Consortium, et al., "Induced pluripotent stem cells from patients with Huntington's disease show CAG-repeat-expansion-associated phenotypes", Cell Stem Cell 11(2):264-278.

Corti, et al., "Genetic correction of human induced pluripotent stem cells from patients with spinal muscular atrophy,", Sci Transl Med 4 (165): I 65ral 62.

Deneault, et al., "Complete Disruption of Autism-Susceptibility Genes by Gene Editing Predominantly Reduces Functional Connectivity of Isogenic Human Neurons", Stem Cell Reports 11:1211-25 (2018).

Denton, et al., "Loss of spastin function results in disease-specific axonal defects in human pluripotent stem cel •• based models of hereditary spastic paraplegia", Stem Cells 32(2):414-23.

Dimos, et al., "Induced pluripotent stem cells generated from patients with ALS can be differentiated into motor neurons", Science 321(5893): 1218-2.

Donnelly, et al., "RNA toxicity from the ALS/FTD C9orf72 expansion is mitigated by antisense intervention", Neuron 80(2):415-28.

Du, et al., "Role of Mismatch repair enzymes in GAA-TTC triplet-repeat expansion in Friedreich ataxia induced pluripotent stem cells", J Biol Chem 287(35):29861-29872 (2012).

Ebert, et al., "Induced pluripotent stem cells from a spinal muscular atrophy patient", Nature 457(7227):277-80.

Egawa, et al., "Drug screening for ALS using patient-specific induced pluripotent stem cells", Sci Transl Med 4(145):145ral04.

Fong, et al., "Genetic correction of tauopathy phenotypes in neurons derived from human induced pluripotent stem cells", Stem Cell Reports 1(3): 1-9.

Hall, et al., "Laminin enhances the growth of human neural stem cells in defined culture media", BMC Neurosci 9:71 (2008).

Han, et al., "Constructing and deconstructing stem cell models of neurological disease", Neuron 70(4):626-44.

Harel and Lupski, "Charcot Marie Tooth disease and pathways to molecular based therapies,", Clin Genet DOI: 10.1111/cge.12393.

Hick, et al., "Neurons and cardiomyocytes derived from induced pluripotent stem cells as a model from mitochondrial defects in Friedreich's ataxia", Dis Model Mech 6(3):608-21 (2013).

Higurashi, "A human Dravet syndrome model from patient induced pluripotent stem cells", Mol Brain 6:19.

Israel, et al., "Probing sporadic and familial Alzheimer's disease using induced pluripotent stem cells,", Nature 482 (7384):216-20.

Kiskinis, et al., "Pathways disrupted in human ALS motor neurons identified through genetic correction of mutant SODI", Cell Stem Cell (epub).

Koch, et al., "Excitation-induced ataxin-3 aggregation in neurons from patients with Machado-Joseph disease", Nature 480(7378):543-546.

Kondo, et al., "Modeling Alzheimer's disease with iPSCs reveals stress phenotypes associated with intracellular Abeta and differential drug responsiveness", Cell Stem Cell 12(4):487-496.

Kray, et al., "Timothy syndrome is associated with activity-dependent dendritic retraction in rodent and human neurons,", Nat Neurosci 16(2):201-9.

Ku, et al., "Friedreich's ataxia induced pluripotent stem cells model intergenerational GAA-TTC triplet repeat instability", Cell Stem Cell 7(5):631-7.

Lee, et al., "Modelling pathogenesis and treatment of familial dysautonomia using patient-specific iPSCs", Nature, 461:402-406 (2009).

Liu, et al., "Signaling defects in iPSC-derived fragile X premutation neurons", Hum Mol Genet 21:3795-3805 (2012).

Mahammad, et al., "Giant axonal neuropathy-associated gigaxonin mutations impair intermediate filament protein degredation,", J Clin Invest 123(5): 1964-75.

Marchetto, et al., "A model for neural development and treatment of Rett syndrome using human induced pluripotent stem cells", Cell, 143(4):527-39.

Mazzulli, et al., "Gaucher disease glucocerebrosidase and a-synuclein form a bidirectional pathogenic loop in synucleinopathies", Cell 146(1):37-52 (2011).

Muratore, et al., "The familial Alzheimer's disease APPV7171 mutation alters APP processing and tau expression in iPSC-derived neurons", Human Molecular Genetics, in press.

Nihei, et al., "Enhanced aggregation of androgen receptor in induced pluripotent stem cell-derived neurons from spinal and bulbar muscular atrophy,", J Biol Chem 288(12):8043-52.

Sareen, et al., "Inhibition of apoptosis blocks human motor neuron cell death in a stem cell model of spinal muscular atrophy", PLoS One 7(6):e39113.

Serra, et al., "Microencapsulation Technology: A Powerful Tool for Integrating Expansion and Cryopreservation of Human Embryonic Stem Cells", PLoS One 6:e23212 (2011).

Shcheglovitov, et al., "SHANK3 and IGFI restore synaptic deficits in neurons from 22q 13 deletion syndrome patients", Nature 503(7475):267-71.

Shi, et al., "A human stem cell model of early Alzheimer's disease pathology in Down syndrome", Sci Transl Med 4(124):124ra129.

Shih, et al., "Development of a fully human assay combining NGN2-inducible neurons co-cultured with iPSC-derived astrocytes amenable for electrophysiological studies", Stem Cell Res 54:102386 (2021).

Song, et al., "Neural differentiation of patient specific iPS cells as a novel approach to study the pathophysiology of multiple sclerosis", Stem Cell Res 8(2):259-73.

Wainger, et al., "Intrinsic membrane hyperexcitability of amyotrophic lateral sclerosis patient-derived motor neurons", Cell Reports 7(1): 1-11.

Yang, et al., "A small molecule screen in stem-cell-derived motor neurons identifies a kinase inhibitor as a candidate therapeutic for ALS", Cell Stem Cell 12(6):713-726.

Zhang, et al., "Rapid single-step induction of functional neurons from human pluripotent stem cells", Neuron 78(5):785-798.

(56)　　　　　References Cited

OTHER PUBLICATIONS

Liu et al, 2012, Efficient and specific modifications of the *Drosophila* genome by means of an easy TALEN strategy, J. Genet. Genomics 39:209-215.

Joung & Sander, 2013, TALENs: a widely applicable technology for targeted genome editing, Nat Rev Mol Cell Bio 14:49-55.

Chang et al., 2013, Genome editing with RNA•guided Cas9 nuclease in zebrafish embryos, Cell Res 23 :465-472.

Hwang et al., 2013, Efficient genome editing in zebrafish using a CRISPR-Cas system, Nat. Biotechnol 31 :227-229.

Xiao et al., 2013, Chromosomal deletions and inversions mediated by TALENS and CRISPR/Cas in zebrafish, Nucl Acids Res 1-11.

Beerli & Barbas, 2002, Engineering polydactyl zinc-finger transcription factors, Nat. Biotechnol, 20: 135-141.

Pabo et al., 2001, Design and selection of novel Cys2His2 zinc finger proteins, Ann. Rev. Biochem 70:313-340.

Isalan et al., 2001, A rapid generally applicable method to engineer zinc fingers illustrated by targeting the HIV-I promoter, Nat. Biotechnol 19:656-660.

Santiago et al., 2008, Targeted gene knockout in mammalian cells by using engineered zinc-finger nucleases, PNAS 105:5809-5814.

Sakai et al., 2001, Design and characterization of a DNA encoded, voltage-sensitive fluorescent protein, Euro J Neuroscience 13 :2314-2318.

Murata et al., 2005, Phosphoinositide phosphatase activity coupled to an intrinsic voltage sensor, Nature 435:1239-1243.

Chanda et al., 2005, A hybrid approach to measuring electrical activity in genetically specified neurons, Nat Neuroscience 8: 1619-1626.

Kralj et al, 2012, Optical recording of action potentials in mammalian neurons using a microbial rhodopsin, Nat Methods 9:90-95.

Carlson and Campbell, 2013, Circular permutated red fluorescent proteins and calcium ion indicators based on mCherry, Protein Eng Des Sel 26(12):763-772.

Klapoetke et al., 2014, Independent optical excitation of distinct neural populations, Nat Meth Advance Online Publication 1-14.

Gingrich and Roder, 1998, Inducible gene expression in the nervous system of transgenic mice, Annu Rev Neurosci 21 :377-405.

Wardill et al., 2013, A neuron-based screening platform for optimizing genetically-encoded calcium indicators, PLoS One 8(10):e77728.

Dottori, et al., Neural development in human embryonic stem cells-applications of lentiviral vectors, J Cell Biochem 112(8): 1955-62.

Diester et al., 2011, An optogenetic toolbox designed for primates, Nat Neurosci 14(3):387-97.

Atasoy et al., 2009, A Flex switch targets channelrhodopsin-2 to multiple cell types for imaging and Ion••range circuit mapping, J Neurosci 28(28):7025-7030.

Rothermel et al., 2013, Transgene expression in target-defined neuron populations mediated by retrograde infection with adeno-associated viral vectors, J Neurosci 33(38): 195-206.

Williams et al.: "Scalable Measurements of Intrinsic Excitability in Human iPS Cell-Derived Excitatory Neurons Using All-Optical Electrophysiology", Neurochemical Research, (2019), vol. 44, pp. 714-725.

Zhang et al.: "Chronic optogenetic induction of stress granules is cytotoxic and reveals the evolution of ALS-FTD pathology", eLife, (2019), vol. 8, e39578, pp. 1-23.

* cited by examiner

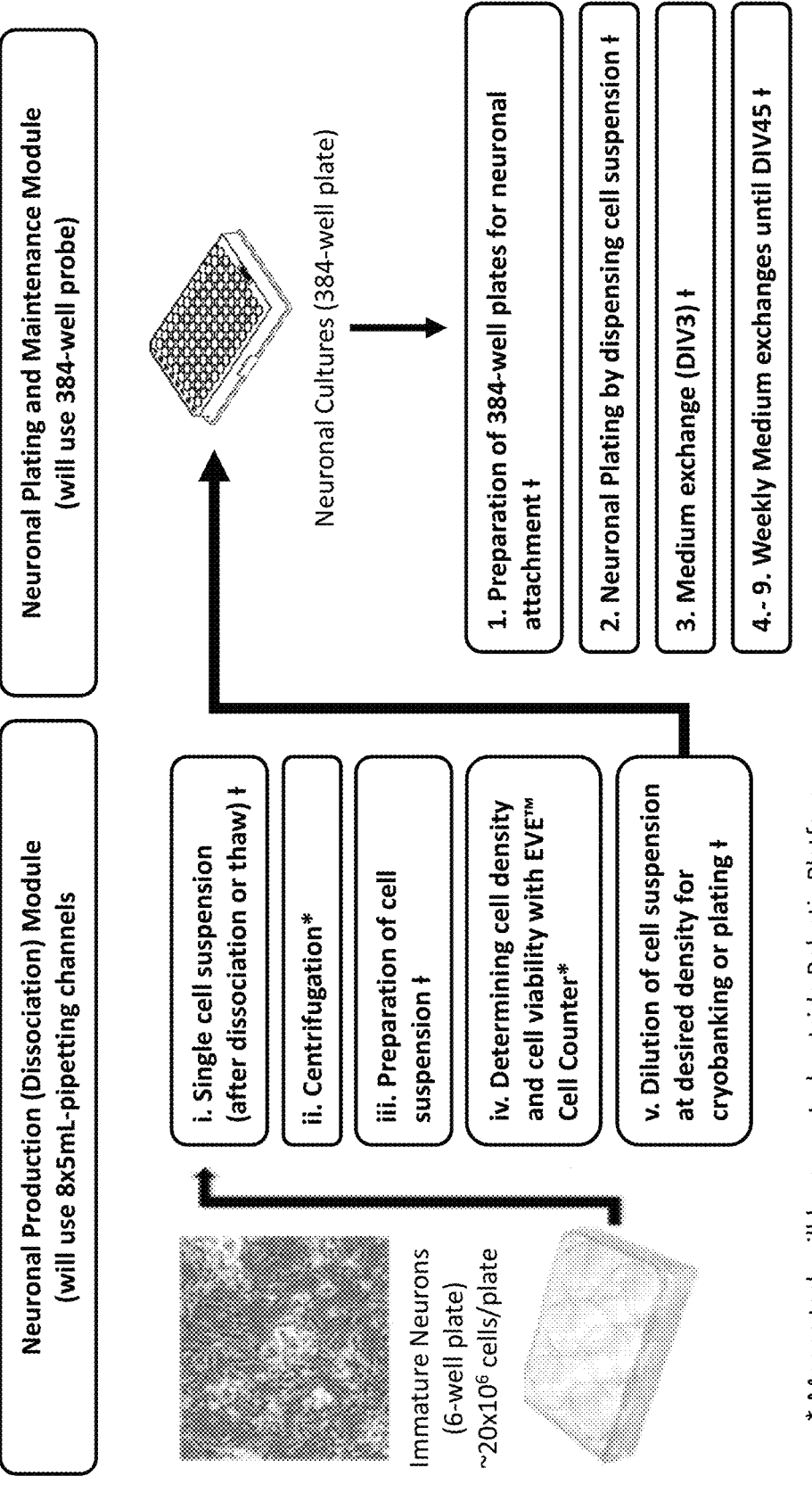

Neuronal Plating and Maintenance Module
(will use 384-well probe)

Neuronal Cultures (384-well plate)

1. Preparation of 384-well plates for neuronal attachment ‡

2. Neuronal Plating by dispensing cell suspension ‡

3. Medium exchange (DIV3) ‡

4.~ 9. Weekly Medium exchanges until DIV45 ‡

Neuronal Production (Dissociation) Module
(will use 8x5mL-pipetting channels)

i. Single cell suspension (after dissociation or thaw) ‡ ii. Centrifugation* iii. Preparation of cell suspension ‡ iv. Determining cell density and cell viability with EVE™ Cell Counter* v. Dilution of cell suspension at desired density for cryobanking or plating ‡

Immature Neurons (6-well plate) ~20x10$^6$ cells/plate

\* Means task will be executed outside Robotic Platform

‡ means task will be executed inside Robotic Platform

FIG. 2

METHODS FOR PRODUCING NEURAL CELLS

FIELD OF THE INVENTION

The invention generally relates to producing neuronal cells for use in biological assays.

BACKGROUND

There is significant scientific and medical interest in the conversion of pluripotent stem cells (PSC) into neurons so that healthy and disease-type neurons can be studied. In some approaches, fibroblasts from patients with poorly understood diseases, such as schizophrenia or Alzheimer's disease, are converted into induced pluripotent stem cells (iPSC) that are then differentiated into neurons to study the pathogenesis of these diseases. Available methods for differentiating stem cells and somatic cells into neurons are unsatisfactory.

Many existing techniques have shown poor yield, create neurons with limited ability to form synapses, and provided inconsistent results when used across in vitro assays.

Generating neurons by differentiation of PSCs can take months. Moreover, many existing techniques for creating neural cells from PSCs do not include the ability to preserve, expand, or prolong the culture of the PSCs or differentiated neural cells at an industrial scale sufficient for high-through-put assays. Thus, PSCs must be continually prepared, cultured and differentiated every time neural cells are needed. As the entire process for preparing sufficiently mature neural cells from PSCs can take months, the current techniques cause a bottleneck in neurological studies.

SUMMARY

The present invention provides differentiated neural cells and methods for making differentiated neural cells from pluripotent stem cells (PSC) at an industrial scale sufficient for high-throughput assays. Methods of the invention allow billions of PSCs and/or neural cells differentiated from the PSCs to be cryopreserved and expanded at multiple steps. Thus, unlike existing methods for producing neural cells from PSCs, the present invention eliminates the need to start the process from the beginning to create new cell lines whenever they are required for use in an assay. As existing methods for differentiating PSCs into neural cells typically take upwards of three months to complete, the present invention dramatically alleviates this bottleneck in neurological studies. In fact, the invention may reduce the full-time equivalent (FTE) cost of producing differentiated neural cells by 50% or more, reduce reagent costs by a factor of at least 4×, and increase throughput to industrial scale levels.

Moreover, methods of the invention provide the ability to prolong the culture of differentiated neural cells by 30-60 days. This extends the useful life of the neural cells, which increases their availability for use in assays. Moreover, prolonging the culture also ensures that a sufficient number of the cells have adequate time to fully mature. For example, neural cells used in intrinsic excitability assays can take about 30 days to mature, while those for synaptic assays can take upwards of 45 days.

Further, as explained in greater detail herein, the present Inventors discovered that the methods of the invention may be used to produce a variety of neural cell types, including those exhibiting a variety of neural conditions. The cells produce consistent and repeatable results across assays, which makes them particularly suitable for use as models. Moreover, despite cryopreservation, the PSC-derived neural cells are robust, and have shown to be plated with a viability greater than 80% after being thawed.

In certain aspects, these differentiated neural cells are cellular disease models. For example, the invention provides methods in which PSCs are differentiated into functional neurons by forced expression of a transcription factor and then also caused to express optogenetic reporters or actuators of neural activity. In certain methods, a gene encoding a transcription factor such as Neurogenin-2 (Ngn2) or Neu-roD1 is introduced into a PSC, e.g., by transfecting a genetic construct. Expression of the transcription factor causes the cell to differentiate into a neuron. Additionally or separately, an optogenetic construct that includes one or more optical reporters and/or optical actuators of cellular activity is introduced into the differentiated neurons. The resulting optogenetic neurons can be made with good yield and readily form synapses to provide a model system for studying healthy and disease-type neurons for a variety of conditions.

In certain aspects, the cells have disease-associated genotypes, and the function and phenotype of the cells may be studied using optogenetic techniques. The differentiated neurons may be derived from a somatic cell from a patient suffering from a neuronal disease. Alternatively, disease-associated genotypes are introduced into a neuron through genome-editing, for example, using a CRISPR/Cas9 system.

In certain aspects, the invention provides methods for producing neuronal cells from PSCs. An exemplary method includes obtaining pluripotent stem cells and introducing an inducible genetic element into the cells that encodes a pro-neuronal transcription factor. The genetic element is then induced causing expression of the transcription factor which differentiates the PSCs into neuronal cells. The differentiated neuronal cells are then cryopreserved.

Preferably, the transcription factor is Neurogenin-2 (Ngn2).

In the methods of the disclosure, the cryopreserved neural cells may be thawed and used in a variety of neural assays. In an exemplary method, the thawed neural cells are cultured. The thawed cells may be co-cultured with glial cells.

In exemplary methods the thawed neural cells are cultured for at least 30-60 days, to produce mature neurons, which represents a prolonged culture relative to existing techniques for generating neurons.

The thawed neuronal cells may be plated and cultured in laminin coated wells of a multi-well plate. In certain aspects, the cells are cultured in a medium supplemented with laminin. This medium may be replaced a number of times during the culture, with every replacement using a medium with a reduced laminin concentration. The Inventors discovered that culturing with a medium supplemented with lami-nin reduces unwanted attachment of the cells to the wells of the plate.

In certain aspects, the thawed neuronal cells are matured using one or more of organoids, 3D cell cultures, and injecting the neural cells into the brain of an animal to induce maturity.

An exemplary method of the invention includes transfecting the pluripotent stem cells with a plasmid encoding a nuclease and guide RNA. The guide RNA and endonuclease are used, for example, to cause at least one knock-in or knockout mutation in the resulting neural cells. In certain aspects, the mutation causes the differentiated neuronal cells to exhibit a phenotype associated with a neural disorder. In certain aspects, the mutation is a KCNQ2 loss-of-function mutation.

In certain methods, the pluripotent stem cells are induced pluripotent stem cells derived from cells obtained from a subject.

The invention also provides methods that include introducing one or more additional genetic constructs into the differentiated neuronal cells such that they express one or more optical reporters of cellular activity and/or optical actuators of cellular activity.

In certain aspects, exemplary methods of the invention further include expanding the pluripotent stem cells prior to the introducing step and/or the inducing step. This intermediate step of expanding the PSCs that have been genetically modified with a pro-neuronal inducible construct allows for the production of millions of PSCs that already contain the genetic expression construct but have not yet been induced, thereby increasing the staring material for neuronal induction by thousands of fold and allowing the yield of neuronal production to reach billions of neurons.

In certain methods, the conversion efficiency of the pluripotent stem cells with the pro-neuronal inducible construct is enhanced by combining the induction of the pro-neuronal transcription factor (e.g. NGN2) with small molecule inhibitor-mediated modulation of key developmental pathways such as TGF-β and BMP4 signaling pathways (Dual SMAD inhibition).

Exemplary methods may additionally or separately include cryopreserving and thawing the pluripotent stem cells prior to the introducing step and/or the inducing step.

BRIEF DESCRIPTION OF THE DRAWINGS

FIG. 2 illustrates an automated robotic platform to carryout steps of the methods of the invention.

DETAILED DESCRIPTION

The present invention provides differentiated neural cells and methods for making differentiated neural cells from pluripotent stem cells (PSC) at an industrial scale sufficient for high-throughput assays. The methods of the invention allow billions of PSCs and/or neural cells differentiated from the PSCs to be cryopreserved and expanded at multiple steps.

In certain aspects, the differentiated neural cells are used as cellular disease models. Exemplary methods of the invention for producing disease models include converting PSCs into functional neurons by forced expression of a single transcription factor and causing the neurons to express optogenetic reporters and/or actuators of neural activity. A transcription factor such as neurogenin-2 (Ngn2) introduced into a pluripotent stem cell by transfection is expressed, causing the cell to differentiate into a neuron.

Figure 1:
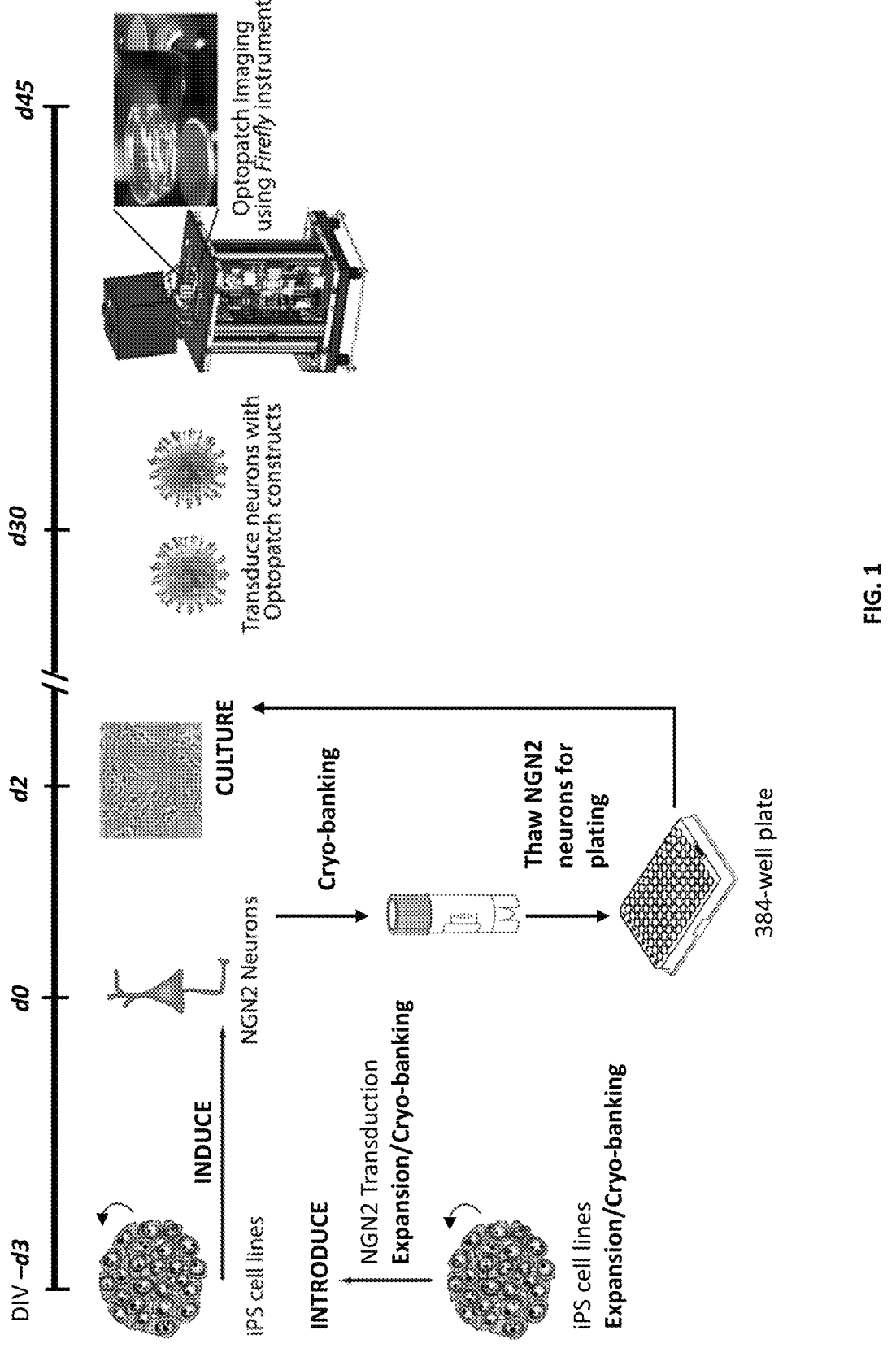
FIG. 1 diagrams an exemplary method for producing PSC-derived neural cells.

FIG. 1 provides an exemplary workflow for generating neuronal cells from PSCs that shows several aspects of the invention. As shown PSCs, in this case, induced PSCs have an inducible genetic construct introduced. A shown, the inducible construct may include a transcription factor, such as Ngn2. Induction of the construct causes the PSCs to express the transcription factor, which differentiates the PSCs into neural cells. In FIG. 1, the neural cells are labeled as Ngn2 neurons.

As also shown in FIG. 1, the present invention provides, for the first time, methods in which the differentiated neural cells are cryopreserved and subsequently thawed. Thus, differentiated neurons may be preserved in industrial quantities, thawed, and modified (e.g., by introducing optogenetic constructs) in accordance with the demands of a particular assay. Preserving the cells in this manner thus eliminates the need to prepare and expand PSCs, introduce and induce the inducible construct, and differentiate the PSCs into neurons. Rather, the neural cells of the present invention are able to be thawed, manipulated, and used on-demand.

After being thawed, the neural cells are, for example, cultured, transduced with optical reporters and actuators, and used in bioassays as a disease model.

FIG. 1 also reveals that the PSCs may be expanded and cryopreserved before and/or after introduction of the inducible construct. As a result, differentiation-ready PSCs may be prepared and preserved in large quantities to quickly differentiate industrial quantities of differentiated neural cells. In certain aspects, such as that shown in FIG. 1, this eliminates the need to prepare and expand induced PSCs from a sample.

Moreover, by preserving the PSCs and/or differentiated neural cells, the present invention permits the use of the same cell line across multiple assays and times. This helps ensure consistency and reproducibility when using the neural cells in bioassays.

In certain aspects, the methods for creating PSC-derived neural cells incorporate production automation to carry out one or more steps, for example, using a robot platform.

FIG. 2 provides an overview of a method for cryopreserving PSC-derived neural cells. In the exemplary method, a robotic platform that includes a neuronal production (dissociation) module with multiple pipette channels is used to create a single cell suspension of immature PSC-derived neural cells. As shown, these neural cells may have been previously cryopreserved. The module dissociates the cells to create the suspension. After centrifugation, the robotic platform prepares a second cell suspension. The platform then dilutes the suspension to a desired density amenable, for example, for cryopreservation and/or plating in a multi-well plate.

As also shown in FIG. 2, a neural plating and maintenance module prepares a multi-well plate for neuronal attachment. This may, for example, include providing a laminin coating. The module then places the cell suspension in the wells of the plate. Subsequently, the module performs one or more cell medium changes. The medium may be supplemented with laminin, which is reduced in concentration during each medium replacement.

The presently disclosed methods may be used to differentiate PSCs into a number of different neural cells types, including, for example, motor neurons, inhibitory neurons, sensory neurons, dopaminergic neurons, medium spiny neurons, human glia co-cultured with neurons, microglial cells, and cardiomyocytes.

In certain aspects, cells may be obtained as pluripotent stem cells or as somatic cells from a subject (e.g., fibroblasts or blood), which can then be converted into induced pluripotent stem cells (iPSCs) for differentiation into neural cells.

For example, certain methods of the invention include obtaining cells from a person suspected of having the condition. Any suitable condition such as a genetic disorder, mental or psychiatric condition, neurodegenerative disease, or neurodevelopmental disorder may be evaluated. Additionally, methods of the invention and the analytical pipelines described herein may be applied to any condition for which an electrophysiological phenotype has been developed.

Exemplary neurodegenerative diseases include Alzheimer's disease, as well as frontotemporal lobar degeneration, Huntington's disease, multiple sclerosis, spinal and bulbar muscular atrophy, and amyotrophic lateral sclerosis. Exemplary mental and psychiatric conditions include schizophrenia. Exemplary genetic disorders, including neurodevelopmental disorders, suitable for analysis by a pipeline defined by methods of the invention include Cockayne syndrome, Down Syndrome, Dravet syndrome, familial dysautonomia, Fragile X Syndrome, Rett Syndrome, Friedreich's ataxia, Gaucher disease, hereditary spastic paraplegias, Machado-Joseph disease (also called spinocerebellar ataxia type 3), Phelan-McDermid syndrome (PMDS), polyglutamine (polyQ)-encoding CAG repeats, giant axonal neuropathy, Charcot-Marie-Tooth disease, a variety of ataxias including spinocerebellar ataxias, spinal muscular atrophy, Timothy syndrome, and various genetic forms of Developmental and Epileptic Encephalopathies caused by mutations in different genes including STXBP1, SCN8A, and KCNQ2. Electrophysiological phenotypes for a variety of conditions have been developed and reported in the literature.

In one illustrative example, fibroblasts may be taken from a patient known or suspected to have a disease. Any suitable cell may be obtained and any suitable method of obtaining a sample may be used. In certain aspects, a dermal biopsy is performed to obtain dermal fibroblasts. The patient's skin may be cleaned and given an injection of local anesthetic. Once the skin is completely anesthetized, a sterile 3 mm punch is used. The clinician may apply pressure and use a "drilling" motion until the punch has pierced the epidermis. The punch will core a 3 mm cylinder of skin. The clinician may use forceps to lift the dermis of the cored skin and a scalpel to cut the core free. The biopsy sample may be transferred to a sterile BME fibroblast medium after optional washing with PBS and evaporation of the PBS. The biopsy site on the patient is dressed (e.g., with an adhesive bandage). Suitable methods and devices for obtaining the cells are discussed in U.S. Pat. Nos. 8,603,809; 8,403,160; 5,591,444; U.S. Pub. 2012/0264623; and U.S. Pub. 2012/0214236, the contents of each of which are incorporated by reference. Any tissue culture technique that is suitable for the obtaining and propagating biopsy specimens may be used such as those discussed in Freshney, Ed., 1986, Animal Cell Culture: A Practical Approach, IRL Press, Oxford England; and Freshney, Ed., 1987, Culture of Animal Cells: A Manual of Basic Techniques, Alan R. Liss & Co., New York, both incorporated by reference.

Cockayne syndrome is a genetic disorder caused by mutations in the ERCC6 and ERCC8 genes and characterized by growth failure, impaired development of the nervous system, photosensitivity, and premature aging. Cockayne syndrome is discussed in Andrade et al., 2012, Evidence for premature aging due to oxidative stress in iPSCs from Cockayne syndrome, Hum Mol Genet 21:3825-3834, the contents of which are incorporated by reference.

Down syndrome is a genetic disorder caused by the presence of all or part of a third copy of chromosome 21 and associated with delayed growth, characteristic facial features, and intellectual disability. Down Syndrome is discussed in Shi et al., 2012, A human stem cell model of early Alzheimer's disease pathology in Down syndrome, Sci Transl Med 4(124):124ra129, the contents of which are incorporated by reference.

Dravet syndrome, also known as Severe Myoclonic Epilepsy of Infancy (SMEI), is a form of intractable epilepsy that begins in infancy and is often associated with mutations in the SCN1A gene or certain other genes such as SCN9A, SCN2B, PCDH19 or GABRG2. Dravet syndrome is discussed in Higurashi et al., 2013, A human Dravet syndrome model from patient induced pluripotent stem cells, Mol Brain 6:19, the contents of which are incorporated by reference.

Familial dysautonomia is a genetic disorder of the autonomic nervous system caused by mutations in the IKBKAP gene and that affects the development and survival of sensory, sympathetic and some parasympathetic neurons in the autonomic and sensory nervous system resulting in variable symptoms including: insensitivity to pain, inability to produce tears, poor growth, and labile blood pressure. Familial dysautonomia is discussed in Lee et al., 2009, Modelling pathogenesis and treatment of familial dysautonomia using patient-specific iPSCs, Nature 461:402-406, the contents of which are incorporated by reference.

Fragile X syndrome is a genetic condition caused by mutations in the FMR1 gene and that causes a range of developmental problems including learning disabilities and cognitive impairment. Fragile X Syndrome is discussed in Liu et al., 2012, Signaling defects in iPSC-derived fragile X premutation neurons, Hum Mol Genet 21:3795-3805, the contents of which are incorporated by reference.

Friedreich ataxia is an autosomal recessive ataxia resulting from a mutation of a gene locus on chromosome 9. The ataxia of Friedreich's ataxia results from the degeneration of nerve tissue in the spinal cord, in particular sensory neurons essential (through connections with the cerebellum) for directing muscle movement of the arms and legs. The spinal cord becomes thinner and nerve cells lose some of their myelin sheath. Friedreich's ataxia is discussed in Ku et al., 2010, Friedreich's ataxia induced pluripotent stem cells model intergenerational GAA-TTC triplet repeat instability, Cell Stem Cell 7(5):631-7; Du et al., 2012, Role of mismatch repair enzymes in GAA.TTC triplet-repeat expansion in Friedreich ataxia induced pluripotent stem cells, J Biol Chem 287(35):29861-29872; and Hick et al., 2013, Neurons and cardiomyocytes derived from induced pluripotent stem cells as a model for mitochondrial defects in Friedreich's ataxia, Dis Model Mech 6(3):608-21, the contents of each of which are incorporated by reference.

Gaucher's disease is a genetic disease caused by a recessive mutation in a gene located on chromosome 1 and in which lipids accumulate in the body. Gaucher disease is discussed in Mazzulli et al., 2011, Gaucher disease glucocerebrosidase and α-synuclein form a bidirectional pathogenic loop in synucleinopathies, Cell 146(1):37-52, the contents of which are incorporated by reference.

Hereditary Spastic Paraplegia (HSP)—also called Familial Spastic Paraplegias, French Settlement Disease, or Strumpell-Lorrain disease—refers to a group of inherited diseases characterized by axonal degeneration and dysfunction resulting in stiffness and contraction (spasticity) in the lower limbs. Hereditary spastic paraplegias is discussed in Denton et al., 2014, Loss of spastin function results in disease-specific axonal defects in human pluripotent stem cell-based models of hereditary spastic paraplegia, Stem Cells 32(2):414-23, the contents of which are incorporated by reference.

Spinocerebellar ataxia type 3 (SCA3), also known as Machado-Joseph disease, is a neurodegenerative disease, an autosomal dominantly inherited ataxia characterized by the slow degeneration of the hindbrain. Machado-Joseph disease (also called spinocerebellar ataxia type 3) is discussed in Koch et al., 2011, Excitation-induced ataxin-3 aggregation in neurons from patients with Machado-Joseph disease, Nature 480(7378):543-546, the contents of which are incorporated by reference.

Phelan-McDermid Syndrome (PMDS) is a progressive neurodevelopmental disorder resulting from mutations in or deletions of the neural protein, Shank3 and characterized by developmental delay, impaired speech, and autism. Phelan-McDermid syndrome (PMDS) is discussed in Shcheglovitov et al., 2013, SHANK3 and IGF1 restore synaptic deficits in neurons from 22q13 deletion syndrome patients, Nature 503(7475):267-71, the contents of which are incorporated by reference.

Trinucleotide repeat disorders are characterized by polyglutamine (polyQ)-encoding CAG repeats. Trinucleotide repeat disorders refer to a set of genetic disorders caused by trinucleotide repeat expansion, which disorders include dentatorubropallidoluysian atrophy, Huntington's disease, spinobulbar muscular atrophy, Spinocerebellar ataxia Type 1, Spinocerebellar ataxia Type 2, Spinocerebellar ataxia Type 3 or Machado-Joseph disease, Spinocerebellar ataxia Type 6, Spinocerebellar ataxia Type 7, and Spinocerebellar ataxia Type 17, as well as a variety of other ataxias. Trinucleotide repeat disorders are discussed in HD iPSC Consortium, 2012, Induced pluripotent stem cells from patients with Huntington's disease show CAG-repeat-expansion-associated phenotypes. Cell Stem Cell 11(2):264-278, the contents of which are incorporated by reference.

Giant axonal neuropathy is a neurological disorder that causes disorganization of neurofilaments, which form a structural framework to define the shape and size of neurons. Giant axonal neuropathy results from mutations in the GAN gene, which codes for the protein gigaxonin. See Mahammad et al., 2013, Giant axonal neuropathy-associated gigaxonin mutations impair intermediate filament protein degradation, J Clin Invest 123(5):1964-75.

Charcot Marie Tooth disease, also known as hereditary motor and sensory neuropathy (HMSN) and peroneal muscular atrophy (PMA), refers to several inherited disorders of the peripheral nervous system characterized by progressive loss of muscle and sensation. See, e.g., Harel and Lupski, 2014, Charcot Marie Tooth disease and pathways to molecular based therapies, Clin Genet DOI: 10.1111/cge.12393.

Spinal muscular atrophy (SMA) is genetic disease caused by mutations in the SMN1 gene, which encodes the survival of motor neuron protein (SMN), the diminished abundance of which neurons results in death of neuronal cells in the spinal cord and system-wide atrophy. Spinal muscular atrophy is discussed in Ebert et al., 2009, Induced pluripotent stem cells from a spinal muscular atrophy patient, Nature 457(7227):277-80; Sareen et al., 2012, Inhibition of apoptosis blocks human motor neuron cell death in a stem cell model of spinal muscular atrophy. PLoS One 7(6):e39113; and Corti et al., 2012, Genetic correction of human induced pluripotent stem cells from patients with spinal muscular atrophy, Sci Transl Med 4 (165):165ra162, the contents of each of which are incorporated by reference.

Timothy syndrome is a genetic disorder arising from a mutation in the Ca(v)1.2 Calcium Channel gene called CACNA1C and characterized by a spectrum of problems that include an abnormally prolonged cardiac "repolarization" time (long QT interval) and other neurological and developmental defects, including heart QT-prolongation, heart arrhythmias, structural heart defects, syndactyly and autism spectrum disorders. Timothy syndrome is discussed in Krey et al., 2013, Timothy syndrome is associated with activity-dependent dendritic retraction in rodent and human neurons, Nat Neurosci 16(2):201-9, the contents of which are incorporated by reference.

Mental and psychiatric disorders such as schizophrenia and autism may involve cellular and molecular defects amenable to study via stem cell models and may be caused by or associated with certain genetic components that can be isolated using methods herein. Schizophrenia is discussed in Brennand et al., 2011, Modelling schizophrenia using human induced pluripotent stem cells, Nature 473(7346):221-225; and Chiang et al., 2011, Integration-free induced pluripotent stem cells derived from schizophrenia patients with a DISC1 mutation, Molecular Psych 16:358-360, the contents of each of which are incorporated by reference.

Alzheimer's disease is a neurodegenerative disease of uncertain cause (although mutations in certain genes have been linked to the disorder) and is one of the most common forms of dementia. Alzheimer's disease is discussed in Israel et al., 2012, Probing sporadic and familial Alzheimer's disease using induced pluripotent stem cells, Nature 482 (7384):216-20; Muratore et al., 2014, The familial Alzheimer's disease APPV717I mutation alters APP processing and tau expression in iPSC-derived neurons, Human Molecular Genetics, in press; Kondo et al., 2013, Modeling Alzheimer's disease with iPSCs reveals stress phenotypes associated with intracellular Abeta and differential drug responsiveness, Cell Stem Cell 12(4):487-496; and Shi et al., 2012, A human stem cell model of early Alzheimer's disease pathology in Down syndrome, Sci Transl Med 4(124):124ra129, the contents of each of which are incorporated by reference.

Frontotemporal lobar degeneration (FTLD) is the name for a group of clinically, pathologically and genetically heterogeneous disorders including frontotemporal dementia (which subdivides to include behavioral-variant frontotemporal dementia (bvFTLD); semantic dementia (SD); and progressive nonfluent aphasia (PNFA)) associated with atrophy in the frontal lobe and temporal lobe of the brain. Frontotemporal lobar degeneration is discussed in Almeida et al, 2013, Modeling key pathological features of frontotemporal dementia with C9ORF72 repeat expansion in iPSC-derived human neurons, Acta Neuropathol 126(3):385-399; Almeida et al., 2012, Induced pluripotent stem cell models of progranulin-deficient frontotemporal dementia uncover specific reversible neuronal defects, Cell Rep 2(4):789-798; and in Fong et al., 2013, Genetic correction of tauopathy phenotypes in neurons derived from human induced pluripotent stem cells, Stem Cell Reports 1(3):1-9, the contents of each of which are incorporated by reference.

Huntington's disease is an inherited disease that causes the progressive degeneration of nerve cells in the brain and is caused by an autosomal dominant mutation in either of an individual's two copies of a gene called Huntingtin (HTT) located on the short arm of chromosome 4. Huntington's disease is discussed in HD iPSC Consortium, 2012, Induced pluripotent stem cells from patients with Huntington's disease show CAG-repeat-expansion-associated phenotypes. Cell Stem Cell 11(2):264-278; An et al., 2012, Genetic correction of Huntington's disease phenotypes in induced pluripotent stem cells, Cell Stem Cell 11(2):253-263; and Camnasio et al., 2012, The first reported generation of several induced pluripotent stem cell lines from homozygous and heterozygous Huntington's disease patients demonstrates mutation related enhanced lysosomal activity, Neurobiol Dis 46(1):41-51, the contents of each of which are incorporated by reference.

Multiple sclerosis is a neurodegenerative disease in which the insulating covers of nerve cells in the brain and spinal cord are damaged. Multiple sclerosis is discussed in Song et al., 2012, Neural differentiation of patient specific iPS cells as a novel approach to study the pathophysiology of multiple sclerosis, Stem Cell Res 8(2):259-73, the contents of which are incorporated by reference.

Spinal and bulbar muscular atrophy (SBMA), also known as spinobulbar muscular atrophy, bulbo-spinal atrophy, X-linked bulbospinal neuropathy (XBSN), X-linked spinal muscular atrophy type 1 (SMAX1), and Kennedy's disease (KD)—is a neurodegenerative disease associated with mutation of the androgen receptor (AR) gene and that results in muscle cramps and progressive weakness due to degeneration of motor neurons in the brain stem and spinal cord. Spinal and bulbar muscular atrophy is discussed in Nihei et al., 2013, Enhanced aggregation of androgen receptor in induced pluripotent stem cell-derived neurons from spinal and bulbar muscular atrophy, J Biol Chem 288(12):8043-52, the contents of which are incorporated by reference.

Rett syndrome is a neurodevelopmental disorder generally caused by a mutation in the methyl CpG binding protein 2, or MECP2, gene and which is characterized by normal early growth and development followed by a slowing of development, loss of purposeful use of the hands, distinctive hand movements, slowed brain and head growth, problems with walking, seizures, and intellectual disability. Rett syndrome is discussed in Marchetto et al., 2010, A model for neural development and treatment of Rett syndrome using human induced pluripotent stem cells, Cell, 143(4):527-39 and in Ananiev et al., 2011, Isogenic pairs of wild type and mutant induced pluripotent stem cell (iPSC) lines from Rett syndrome patients as in vitro disease model, PLoS One 6(9):e25255, the contents of each of which are incorporated by reference.

Amyotrophic lateral sclerosis (ALS), often referred to as "Lou Gehrig's Disease," is a neurodegenerative disease associated with the progressive degeneration and death of the motor neurons and a resultant loss of muscle control or paralysis. Amyotrophic lateral sclerosis is discussed in Kiskinis et al., 2014, Pathways disrupted in human ALS motor neurons identified through genetic correction of mutant SOD1, Cell Stem Cell (epub); Wainger et al., 2014, Intrinsic membrane hyperexcitability of amyotrophic lateral sclerosis patient-derived motor neurons, Cell Reports 7(1):1-11; Donnelly et al., 2013, RNA toxicity from the ALS/FTD C9orf72 expansion is mitigated by antisense intervention, Neuron 80(2):415-28; Alami, 2014, Microtubule-dependent transport of TDP-43 mRNA granules in neurons is impaired by ALS-causing mutations, Neuron 81(3):536-543; Donnelly et al., 2013, RNA toxicity from the ALS/FTD C9ORF72 expansion is mitigated by antisense intervention, Neuron 80(2):415-428; Bilican et al, 2012, Mutant induced pluripotent stem cell lines recapitulate aspects of TDP-43 proteinopathies and reveal cell-specific vulnerability, PNAS 109(15):5803-5808; Egawa et al., 2012, Drug screening for ALS using patient-specific induced pluripotent stem cells, Sci Transl Med 4(145):145ra104; and in Yang et al., 2013, A small molecule screen in stem-cell-derived motor neurons identifies a kinase inhibitor as a candidate therapeutic for ALS, Cell Stem Cell 12(6):713-726, the contents of each of which are incorporated by reference.

In exemplary methods of the invention, cells are obtained from a patient, converted into PSCs, which are differentiated into specific neural subtypes. An exemplary method includes obtaining somatic cells and reprogramming the cells into induced pluripotent stem cells (iPSCs) using known methods such as the use of defined transcription factors. The iPSCs are characterized by their ability to proliferate indefinitely in culture while preserving their developmental potential to differentiate into derivatives of all three embryonic germ layers. In certain aspects, fibroblasts are converted to iPSC by methods such as those discussed in Takahashi and Yamanaka, 2006, Induction of pluripotent stem cells from mouse embryonic and adult fibroblast cultures by defined factors Cell 126:663-676.; and Takahashi, et al., 2007, Induction of pluripotent stem cells from adult human fibroblasts by defined factors, Cell 131:861-872.

Induction of pluripotent stem cells from adult fibroblasts can be done by methods that include introducing four factors, Oct3/4, Sox2, c-Myc, and Klf4, under embryonic stem (ES) cell culture conditions. Human dermal fibroblasts (HDF) are obtained. Retroviruses containing human Oct3/4, Sox2, Klf4, and c-Myc are introduced into the HDF. Six days after transduction, the cells are harvested by trypsinization and plated onto mitomycin C-treated SNL feeder cells. See, e.g., McMahon and Bradley, 1990, Cell 62:1073-1085. About one day later, the medium (DMEM containing 10% FBS) is replaced with a primate ES cell culture medium supplemented with 4 ng/mL basic fibroblast growth factor (bFGF). See Takahashi, et al., 2007, Cell 131:861. Later, hES cell-like colonies are picked and mechanically disaggregated into small clumps without enzymatic digestion. Each cell should exhibit morphology similar to that of human ES cells, characterized by large nuclei and scant cytoplasm. The cells after transduction of HDF are human iPS cells. DNA fingerprinting, sequencing, or other such assays may be performed to verify that the iPS cell lines are genetically matched to the donor.

These iPS cells can then be differentiated into specific neuronal subtypes. Pluripotent cells such as iPS cells are by definition capable of differentiating into cell types, characteristic of different embryonic germ layers. A property of both embryonic stem cells human iPS cells is their ability, when plated in suspension culture, to form embryoid bodies (EBs). EBs formed from iPS cells are treated with two small molecules: an agonist of the sonic hedgehog (SHH) signaling pathway and retinoic acid (RA). For more detail, see the methods described in Dimos et al., 2008, Induced pluripotent stem cells generated from patients with ALS can be differentiated into motor neurons, Science 321(5893):1218-21; Amoroso et al., 2013, Accelerated high-yield generation of limb-innervating motor neurons from human stem cells, J Neurosci 33(2):574-86; and Boulting et al., 2011, A functionally characterized test set of human induced pluripotent stem cells, Nat Biotech 29(3):279-286.

When the differentiated EBs are allowed to adhere to a laminin-coated surface, neuron-like outgrowths are observed, which results differentiation into specific neuronal subtypes. Additional relevant discussion may be found in Davis-Dusenbery et al., 2014, How to make spinal motor neurons, Development 141(3):491-501; Sandoe and Eggan, 2013, Opportunities and challenges of pluripotent stem cell neurodegenerative disease models, Nat Neuroscience 16(7): 780-9; and Han et al., 2011, Constructing and deconstructing stem cell models of neurological disease, Neuron 70(4):626-44.

In methods of the invention, iPSCs are converted into neurons. Conversion includes causing a stem cell to express a single transcription factor. Overexpressing a single transcription factor such as neurogenin-2 (Ngn2) rapidly converts ES and iPS cells into neuronal cells. See Zhang et al., 2013, Rapid single-step induction of functional neurons from human pluripotent stem cells, Neuron 78(5):785-798. The transcription factor may be introduced by lentiviral infection (discussed in greater detail below). As reported in Zhang 2013 a puromycin resistance gene may be co-expressed with Ngn2 for selection. ES or iPS cells are plated on day −2, infected with lentiviruses on day −1, and Ngn2 expression is induced on day 0. A 24 hour puromycin selection period is started on day 1, and mouse glia (primarily astrocytes) are added on day 2 to enhance synapse formation. Forced Ngn2 expression converts ES and iPS cells into neuron-like cells in less than one week, and produces an apparently mature neuronal morphology in less than two weeks, as reported in Zhang 2013.

Before or after cryopreservation, differentiated cells such as motor neurons may be dissociated and plated onto glass coverslips coated with poly-d-lysine and laminin. Motor neurons may be fed with a suitable medium such as a neurobasal medium supplemented with N2, B27, GDNF, BDNF, and CTNF. Cells may be maintained in a suitable medium such as an N2 medium (DMEM/F12 [1:1] supplemented with laminin [1 µg/mL; Invitrogen], FGF-2 [10 ng/ml; R&D Systems, Minneapolis, MN], and N2 supplement [1%; Invitrogen]), further supplemented with GDNF, BDNF, and CNTF, all at 10 ng/ml. Suitable media are described in Son et al., 2011, Conversion of mouse and human fibroblasts into functional spinal motor neurons, Cell Stem Cell 9:205-218; Vierbuchen et al., 2010, Direct conversion of fibroblasts to functional neurons by defined factors, Nature 4 63:1035-1041; Kuo et al., 2003, Differentiation of monkey embryonic stem cells into neural lineages, Biology of Reproduction 68:1727-1735; and Wernig et al., 2002, Tau EGFP embryonic stem cells: an efficient tool for neuronal lineage selection and transplantation. J Neuroscience Res 69:918-24, each incorporated by reference.

Methods of the invention may include causing the cell to express an optical reporter, observing a signature generated by the optical reporter, and comparing the observed signature to a control signature. The control signature may be a disease-free cell and can be obtained by obtaining a control cell that is also of the specific neural subtype and is genetically and phenotypically similar to the test cells. In certain embodiments—where, for example, a patient has a known mutation or allele at a certain locus—genetic editing is performed to generate a control cell line that but for the known mutation is isogenic with the test cell line. For example, where a patient is known to have a multiplication of the SNCA gene, genetic editing techniques can introduce a wild-type SNCA gene into the cell line to create a control cell line with a wild-type genotype and phenotype. Additionally, genome editing may be used to introduce a mutation of interest into a neuron in order to evaluate the phenotypic effect of the mutation and to investigate potential links to a disease. Genetic or genome editing techniques may proceed via zinc-finger domain methods, transcription activator-like effector nucleases (TALENs), or clustered regularly interspaced short palindromic repeat (CRISPR) nucleases.

Genome editing techniques (e.g., use of zinc finger domains) may be used to create test and control cells that are isogenic but—for a variant of interest. In certain aspects, genome editing techniques are applied to iPS cells. For example, a second corrected line may be generated using zinc finger domains resulting in two otherwise isogenic lines. After that, diseased and corrected iPS cells may be differentiated into motor neurons using embryoid bodies according to the methods described above.

Genomic editing may be performed by any suitable method known in the art. For example, the chromosomal sequence encoding the target gene of interest may be edited using TALENs technology. TALENS are artificial restriction enzymes generated by fusing a TAL effector DNA binding domain to a DNA cleavage domain. In certain aspects, genome editing is performed using CRISPR technology. TALENs and CRISPR methods provide one-to-one relationship to the target sites, i.e. one unit of the tandem repeat in the TALE domain recognizes one nucleotide in the target site, and the crRNA or gRNA of CRISPR/Cas system hybridizes to the complementary sequence in the DNA target. Methods can include using a pair of TALENs or a Cas9 protein with one gRNA to generate double-strand breaks in the target. The breaks are then repaired via non-homologous end-joining or homologous recombination (HR).

TALENs uses a nonspecific DNA-cleaving nuclease fused to a DNA-binding domain that can be to target essentially any sequence. For TALEN technology, target sites are identified and expression vectors are made. See Liu et al, 2012, Efficient and specific modifications of the *Drosophila* genome by means of an easy TALEN strategy, J. Genet. Genomics 39:209-215. The linearized expression vectors (e.g., by NotI) and used as template for mRNA synthesis. A commercially available kit may be use such as the mMES-SAGE mMACHINE SP6 transcription kit from Life Technologies (Carlsbad, CA). See Joung & Sander, 2013, TALENs: a widely applicable technology for targeted genome editing, Nat Rev Mol Cell Bio 14:49-55.

CRISPR methodologies employ a nuclease, CRISPR-associated (Cas9), that complexes with small RNAs as guides (gRNAs) to cleave DNA in a sequence-specific manner upstream of the protospacer adjacent motif (PAM) in any genomic location. CRISPR may use separate guide RNAs known as the crRNA and tracrRNA. These two separate RNAs have been combined into a single RNA to enable site-specific mammalian genome cutting through the design of a short guide RNA. Cas9 and guide RNA (gRNA) may be synthesized by known methods. Cas9/guide-RNA (gRNA) uses a non-specific DNA cleavage protein Cas9, and an RNA oligo to hybridize to target and recruit the Cas9/gRNA complex. See Chang et al., 2013, Genome editing with RNA-guided Cas9 nuclease in zebrafish embryos, Cell Res 23:465-472; Hwang et al., 2013, Efficient genome editing in zebrafish using a CRISPR-Cas system, Nat. Biotechnol 31:227-229; Xiao et al., 2013, Chromosomal deletions and inversions mediated by TALENS and CRISPR/Cas in zebrafish, Nucl Acids Res 1-11.

In certain aspects, genome editing is performed using zinc finger nuclease-mediated process as described, for example, in U.S. Pub. 2011/0023144 to Weinstein.

Typically, a zinc finger nuclease comprises a DNA binding domain (i.e., zinc finger) and a cleavage domain (i.e., nuclease) and this gene may be introduced as mRNA (e.g., 5' capped, polyadenylated, or both). Zinc finger binding domains may be engineered to recognize and bind to any nucleic acid sequence of choice. See, for example, Beerli & Barbas, 2002, Engineering polydactyl zinc-finger transcription factors, Nat. Biotechnol, 20:135-141; Pabo et al., 2001, Design and selection of novel Cys2His2 zinc finger proteins, Ann. Rev. Biochem 70:313-340; Isalan et al., 2001, A rapid generally applicable method to engineer zinc fingers illustrated by targeting the HIV-1 promoter, Nat. Biotechnol 19:656-660; and Santiago et al., 2008, Targeted gene knockout in mammalian cells by using engineered zinc-finger nucleases, PNAS 105:5809-5814. An engineered zinc finger binding domain may have a novel binding specificity compared to a naturally-occurring zinc finger protein. Engineering methods include, but are not limited to, rational design and various types of selection. A zinc finger binding domain may be designed to recognize a target DNA sequence via zinc finger recognition regions (i.e., zinc fingers). See for example, U.S. Pat. Nos. 6,607,882; 6,534,261 and 6,453, 242, incorporated by reference. Exemplary methods of selecting a zinc finger recognition region may include phage display and two-hybrid systems, and are disclosed in U.S. Pat. Nos. 5,789,538; 5,925,523; 6,007,988; 6,013,453; 6,410,248; 6,140,466; 6,200,759; and 6,242,568, each of which is incorporated by reference. Zinc finger binding domains and methods for design and construction of fusion proteins (and polynucleotides encoding same) are known to those of skill in the art and are described in detail in U.S. Pub. 2005/0064474 and U.S. Pub. 2006/0188987, each incorporated by reference. Zinc finger recognition regions, multi-fingered zinc finger proteins, or combinations thereof may be linked together using suitable linker sequences, including for example, linkers of five or more amino acids in length. See, U.S. Pat. Nos. 6,479,626; 6,903,185; and 7,153,949, incorporated by reference.

In certain aspects, methods for genome editing include introducing into the cell an exchange polynucleotide (typically DNA) with a sequence that is substantially identical to the chromosomal sequence at the site of cleavage and which further comprises at least one specific nucleotide change. Where the cells have been obtained from a subject suspected to have a neurodegenerative disease, a method such as TALENs, CRISPRs, or zinc fingers may be used to make a control cell line. For example, methods may be used to produce a cell line that is isogenic but for a mutation in a gene suspected of an association with a disease. While any such technology may be used, the following illustrates genome editing via zinc finger nucleases.

Using genome editing for modifying a chromosomal sequence, an isogenic (but for the mutation of interest) control line can be generated. In certain aspects, a control cells are obtained from healthy individuals, i.e., without using genome editing on cells taken from the subject. The control line can be used in the analytical methods described herein to generate a control signature for comparison to test data. In certain aspects, a control signature is stored on-file after having been previously generated and stored and the stored control signature is used (e.g., a digital file such as a graph or series of measurements stored in a non-transitory memory in a computer system). For example, a control signature could be generated by assaying a large population of subjects of known phenotype or genotype and storing an aggregate result as a control signature for later downstream comparisons.

The PSC derived neurons and any optional control line may be caused to express an optical reporter of neural or electrical activity. Examples of neural activity include action potentials in a neuron or fusion of vesicles releasing neurotransmitters. Exemplary electrical activity includes action potentials in a neuron, astrocyte or other electrically active cell. Further examples of neural or electrical activity include ion pumping or release or changing ionic gradients across membranes. Causing a cell to express an optical reporter of neural activity can be done with a fluorescent reporter of vesicle fusion. Expressing an optical reporter of neural or electrical activity can include transformation with an optogenetic reporter. For example, the cell may be transformed with a vector comprising an optogenetic reporter and the cell may also be caused to express an optogenetic actuator by transformation. In certain aspects, the differentiated neurons are cultured (e.g., for about 15 days) and then infected with lentivirus bearing a genetically-encoded optical reporter of neural activity and optionally an optical voltage actuator.

Any suitable optical reporter of neural activity may be used. Exemplary reporters include fluorescent reporters of transmembrane voltage differences, pHluorin-based reporters of synaptic vesicle fusion, and genetically encoded calcium indicators. In a preferred embodiment, a genetically encoded voltage indicator is used. Genetically encoded voltage indicators that may be used or modified for use with methods of the invention include FlaSh (Siegel, 1997, A genetically encoded optical probe of membrane voltage. Neuron 19:735-741); SPARC (Ataka, 2002, A genetically targetable fluorescent probe of channel gating with rapid kinetics, Biophys J 82:509-516); and VSFP1 (Sakai et al., 2001, Design and characterization of a DNA encoded, voltage-sensitive fluorescent protein, Euro J Neuroscience 13:2314-2318). A genetically encoded voltage indicator based on the paddle domain of a voltage-gated phosphatase is CiVSP (Murata et al., 2005, Phosphoinositide phosphatase activity coupled to an intrinsic voltage sensor, Nature 435: 1239-1243). Another indicator is the hybrid hVOS indicator (Chanda et al., 2005, A hybrid approach to measuring electrical activity in genetically specified neurons, Nat Neuroscience 8:1619-1626), which transduces the voltage dependent migration of dipicrylamine (DPA) through the membrane leaflet to "dark FRET" (fluorescence resonance energy transfer) with a membrane-targeted GFP.

Optical reporters that may be suitable for use with the invention include those from the family of proteins of known microbial rhodopsins. A reporter based on a microbial rhodopsin may provide high sensitivity and speed. Suitable indicators include those that use the endogenous fluorescence of the microbial rhodopsin protein Archaerhodopsin 3 (Arch) from *Halorubum sodomense*. Arch resolves action potentials with high signal-to-noise (SNR) and low phototoxicity. A mutant form of Arch, D95N, has been shown not to exhibit a hyperpolarizing current associated with some indicators. Other mutant forms of Arch, termed QuasAr1 and QuasAr2, have been shown to exhibit improved brightness, sensitivity to voltage, speed of response, and trafficking to the neuronal plasma membrane. Arch and the above-mentioned variants target eukaryotic membranes and can image single action potentials and subthreshold depolarization in cultured mammalian neurons. See Kralj et al, 2012, Optical recording of action potentials in mammalian neurons using a microbial rhodopsin, Nat Methods 9:90-95. Thus, Arch and variants of Arch such as Arch(D95N) may provide good optical reporters of neural activity according to embodiments of the invention.

In certain aspects, an improved variant of Arch such as QuasAr1 or QuasAr2 is used. QuasAr1 comprises Arch with the mutations: P6OS, T805, D95H, D106H, and F161V. QuasAr2 comprises Arch with the mutations: P6OS, T805, D95Q, D106H, and F161V. Positions Asp95 and Asp106 of Arch (which are structurally aligned with positions Asp85 and Asp96 of bacteriorhodopsin, and have been reported to play key roles in proton translocation during the photo cycle) are targets for modification because they flank the Schiff base in the proton-transport chain and are likely important in determining voltage sensitivity and speed. The other mutations improve the brightness of the protein. Starting with an Arch gene, it may be beneficial to add endoplasmic reticulum (ER) export motifs and a trafficking sequence (TS) according to methods known in the art.

QuasAr1 and QuasAr2 each refer to a specific variant of Arch. As discussed, archaerhodopsin 3 (Arch) functions as a fast and sensitive voltage indicator. Improved versions of Arch include the QuasArs ('quality superior to Arch'), described in Hochbaum et al., 2014. QuasAr1 differs from wild-type Arch by the mutations P6OS, T805, D95H, D106H and F161V. QuasAr2 differed from QuasAr1 by the mutation H95Q. QuasAr1 and QuasAr2 report action potentials (APs).

Arch and the above-mentioned variants target eukaryotic membranes and can image single action potentials and subthreshold depolarization in cultured mammalian neurons. See Kralj et al, 2012, Optical recording of action potentials in mammalian neurons using a microbial rhodopsin, Nat Methods 9:90-95 and Hochbaum et al., All-optical electrophysiology in mammalian neurons using engineered microbial rhodopsins, Nature Methods, 11, 825-833 (2014), both incorporated by reference. Thus Arch and variants of Arch may provide good optical reporters of electrical activity according to embodiments of the invention.

The invention includes introducing optical reporters based on Archaerhodopsins that function in mammalian cells, including human stem cell-derived neurons, into the PSCs or PSC-derived neural cells. These proteins indicate electrical dynamics with sub-millisecond temporal resolution and sub-micron spatial resolution and may be used in non-contact, high-throughput, and high-content studies of electrical dynamics in cells and tissues using optical measurement of membrane potential. These reporters are broadly useful, particularly in eukaryotic, such as mammalian, including human cells.

The invention includes introducing optical reporters based on Archaerhodopsin 3 (Arch 3) and its homologues. Arch 3 is Archaerhodopsin from *H. sodomense* and it is known as a genetically-encoded reagent for high-performance yellow/green-light neural silencing. Gene sequence at GenBank: GU045593.1 (synthetic construct Arch 3 gene, complete cds, submitted Sep. 28, 2009). These proteins localize to the plasma membrane in eukaryotic cells and show voltage-dependent fluorescence.

These optical reporters show high sensitivity. In mammalian cells, Archaerhodopsin-based reporters show about 3-fold increase in fluorescence between −150 mV and +150 mV. The response is linear over most of this range. Membrane voltage can be measured with a precision of <1 mV in a 1 s interval. Reporters of the invention show high speed. QuasAr1 shows 90% of its step response in 0.05 ms. The upstroke of a cardiac AP lasts approximately 1 ms, so the speeds of Arch-derived indicators meet the benchmark for imaging electrical activity. Reporters of the invention show high photo-stability and are comparable to GFP in the number of fluorescence photons produced prior to photobleaching. The reporters may also show far red spectrum. The Arch-derived voltage-indicating protein reporters, sometimes referred to as genetically encoded voltage indicators (GEVIs), may be excited with a laser at wavelengths between 590-640 nm, and the emission is in the near infrared, peaked at 710 nm. The emission is farther to the red than any other existing fluorescent protein. These wavelengths coincide with low cellular auto-fluorescence. This feature makes these proteins particularly useful in optical measurements of action potentials as the spectrum facilitates imaging with high signal-to-noise ratio, as well as multi-spectral imaging in combination with other fluorescent probes.

Other optogenetic reporters may be used with methods and systems of the invention. Suitable optogenetic reporters include the two Arch variants dubbed Archer1 and Archer2 reported in Flytzanis, et al., 2014, Archaerohodopsin variants with enhanced voltage-sensitive fluorescence in mammalian and *Caenorhabditis elegans* neurons, Nat Comm 5:4894, incorporated by reference. Archer1 and Archer2 exhibit enhanced radiance in response to 655 nm light have 3-5 times increased fluorescence and 55-99 times reduced photocurrents compared with Arch WT. Archer1 (D95E and T99C) and Archer2 (D95E, T99C and A225M) may be used for voltage sensing. These mutants exhibit high baseline fluorescence (×3-5 over Arch WT), large dynamic range of sensitivity (85% DF/F and 60% DF/F per 100 mV for Archer1 and Archer2, respectively) that is stable over long illumination times, and fast kinetics, when imaged at ×9 lower light intensity (880 mW mm^-2 at 655 nm) than the most recently reported Arch variants. Archer1's characteristics allow its use to monitor rapid changes in membrane voltage throughout a single neuron and throughout a population of neurons in vitro. Although Archer1 has minimal pumping at wavelengths used for fluorescence excitation (655 nm), it maintains strong proton pumping currents at lower wavelengths (560 nm). Archer1 provides a bi-functional tool with both voltage sensing with red light and inhibitory capabilities with greenlight. Archer1 is capable of detecting small voltage changes in response to sensory stimulus Suitable optogenetic reporters include the Arch-derived voltage sensors with trafficking signals for enhanced localization as well as the Arch mutants dubbed Arch-EEN and Arch-EEQ reported in Gong et al., Enhanced Archaerhodopsin fluorescent protein voltage indicators, PLoSOne 8(6):e66959, incorporated by reference. Such reporters may include variants of Arch with the double mutations D95N-D106E (Arch-EEN) and D95Q-D106E (Arch-EEQ).

Suitable optogenetic reporters include sensors that use fluorescence resonance energy transfer (FRET) to combine rapid kinetics and the voltage dependence of the rhodopsin family voltage-sensing domains with the brightness of genetically engineered protein fluorophores. Such FRET-opsin sensors offer good spike detection fidelity, fast kinetics, and high brightness. FRET-opsin sensors are described in Gong et al., Imaging neural spiking in brain tissue using FRET-opsin protein voltage sensors, Nat Comm 5:3674, incorporated by reference. A suitable FRET-opsin may include a fusion of a bright fluorophore to act as a FRET donor to a Mac rhodopsin molecule to server as both the voltage sensing domain and the FRET acceptor. Other sensors include the Accelerated Sensor of Action Potentials (ASAP1), a voltage sensor formed by insertion of a circularly permuted GFP into a chicken voltage-sensitive phosphatase. St-Pierre, 2014, High-fidelity optical reporting of neuronal electrical activity with an ultrafast fluorescent voltage sensor, Nat Neurosci 17(6):884, incorporated by reference. Other suitable reporters may include the ArcLight-derived probe dubbed Bongwoori and described in Piao et al., 2015, Combinatorial mutagenesis of the voltage-sensing domain enables the optical resolution of action potentials firing at 60 Hz by a genetically encoded fluorescent sensor of membrane potential, J Neurosci 35(1):372-385, incorporated by reference.

In certain aspects, the PSC-derived neurons are transformed with an optical voltage actuator. This can occur, for example, simultaneously with transformation with the vector comprising the optogenetic reporter. The far-red excitation spectrum of the QuasAr reporters suggests that they may be paired with a blue light-activated channelrhodopsin to achieve all-optical electrophysiology. For spatially precise optical excitation, the channelrhodopsin should carry current densities sufficient to induce APs when only a subsection of a cell is excited. Preferably, light used for imaging the reporter should not activate the actuator, and light used for activating the actuator should not confound the fluorescence signal of the reporter. Thus in a preferred embodiment, an optical actuator and an optical reporter are spectrally orthogonal to avoid crosstalk and allow for simultaneous use. Spectrally orthogonal systems are discussed in Carlson and Campbell, 2013, Circular permutated red fluorescent proteins and calcium ion indicators based on mCherry, Protein Eng Des Sel 26(12):763-772.

Preferably, a genetically-encoded optogenetic actuator is used. One actuator is channelrhodopsin2 H134R, an optogenetic actuator described in Nagel, G. et al., 2005, Light activation of channelrhodopsin-2 in excitable cells of *Caenorhabditis elegans* triggers rapid behavioral responses, Curr. Biol. 15, 2279-2284.

A screen of plant genomes has identified an optogenetic actuator, *Scherffelia dubia* ChR (sdChR), derived from a fresh-water green alga first isolated from a small pond in Essex, England. See Klapoetke et al., 2014, Independent optical excitation of distinct neural populations, Nat Meth Advance Online Publication 1-14; see also Melkonian & Preisig, 1986, A light and electron microscopic study of *Scherffelia dubia*, a new member of the scaly green flagellates (Prasinophyceae). Nord. J. Bot. 6:235-256, both incorporated by reference. SdChR may offer good sensitivity and a blue action spectrum.

An improved version of sdChR dubbed CheRiff may be used as an optical actuator. The gene for *Scherffelia dubia* Channelrhodopsin (sdChR) (selected from a screen of channelrhodopsins for its blue excitation peak (474 nm) and its large photocurrent relative to ChR2) is synthesized with mouse codon optimization, a trafficking sequence from Kir2.1 is added to improve trafficking, and the mutation E154A is introduced. CheRiff exhibits significantly decreased crosstalk from red illumination (to $10.5\pm2.8$ pA) allowing its use in cells along with optogenetic reporters described herein. CheRiff shows good expression and membrane trafficking in cultured rat hippocampal neurons. The maximum photocurrent under saturating illumination (488 nm, 500 mW/cm) is $2.0\pm0.1$ nA (n=10 cells), approximately 2-fold larger than the peak photocurrents of ChR2 H134R or ChIEF (Lin et al., 2009, Characterization of engineered channelrhodopsin variants with improved properties and kinetics, Biophys J 96:1803-1814). In neurons expressing CheRiff, whole-cell illumination at only $22\pm10$ mW/cm induces a photocurrent of 1 nA. Compared to ChR2 H134R and to ChIEF under standard channelrhodopsin illumination conditions (488 nm, 500 mW/cm). At 23° C., CheRiff reaches peak photocurrent in $4.5\pm0.3$ ms (n=10 cells). After a 5 ms illumination pulse, the channel closing time constant was comparable between CheRiff and ChIEF ($16\pm0.8$ ms, n=9 cells, and $15\pm2$ ms, n=6 cells, respectively, p=0.94), and faster than ChR2 H134R ($25\pm4$ ms, n=6 cells, p<0.05). Under continuous illumination CheRiff partially desensitizes with a time constant of 400 ms, reaching a steady-state current of $1.3\pm0.08$ nA (n=10 cells). Illumination of neurons expressing CheRiff induces trains of APs with high reliability and high repetition-rate.

When testing for optical crosstalk between QuasArs and CheRiff in cultured neurons, illumination sufficient to induce high-frequency trains of APs (488 nm, 140 mW/cm) perturbed fluorescence of QuasArs by <1%. Illumination with high intensity red light (640 nm, 900 W/cm) induced an inward photocurrent through CheRiff of $14.3\pm3.1$ pA, which depolarized neurons by $3.1\pm0.2$ mV (n=5 cells). ChIEF and ChR2 H134R generated similar red light photocurrents and depolarizations. For most applications this level of optical crosstalk is acceptable.

In certain aspects, it is preferable to use an actuator with an activation that is maximal at a violet light wavelength between 400-440 nm, further to the blue than CheRiff. Violet-activated channelrhodopsins can be simultaneously combined with yellow-excited Ca2+ indicators (e.g. jRCaMP1a, jRGECO 1a, and R-CaMP2) and a red-excited voltage indicator, e.g. QuasAr2, for simultaneous monitoring of Ca2+ and voltage under optical stimulus conditions.

A preferred violet-excited channelrhodopsin actuator is TsChR, derived from *Tetraselmis striata* (See Klapoetke et al., 2014, Independent optical excitation of distinct neural populations, Nat. Meth. 11, 338-346 (2014)). This channelrhodopsin actuator has a blue-shifted action spectrum with a peak at 435 nm. Another preferred violet channelrhodopsin actuator is PsChR, derived from *Platymonas subcordiformis* (see Govorunova, Elena et al., 2013, Characterization of a highly efficient blue-shifted channelrhodopsin from the marine alga *Platymonas subcordiformis*, J Biol Chem 288(41):29911-29922). PsChr has a blue-shifted action spectrum with a peak at 437 nm. PsChR and TsChR are advantageously paired with red-shifted Ca2+ indicators and can be used in the same cell or same field of view as these red-shifted Ca2+ indicators without optical crosstalk.

The optogenetic reporters and actuators may be delivered in constructs described here as Optopatch constructs delivered through the use of an expression vector. Optopatch may be taken to refer to systems that perform functions traditionally associated with patch clamps, but via an optical input, readout, or both as provided for by, for example, an optical reporter or actuator. An Optopatch construct may include a bicistronic vector for co-expression of CheRiff-eGFP and QuasAr1- or QuasAr2-mOrange2. The QuasAr and CheRiff constructs may be delivered separately, or a bicistronic expression vector may be used to obtain a uniform ratio of actuator to reporter expression levels.

Figure 4:
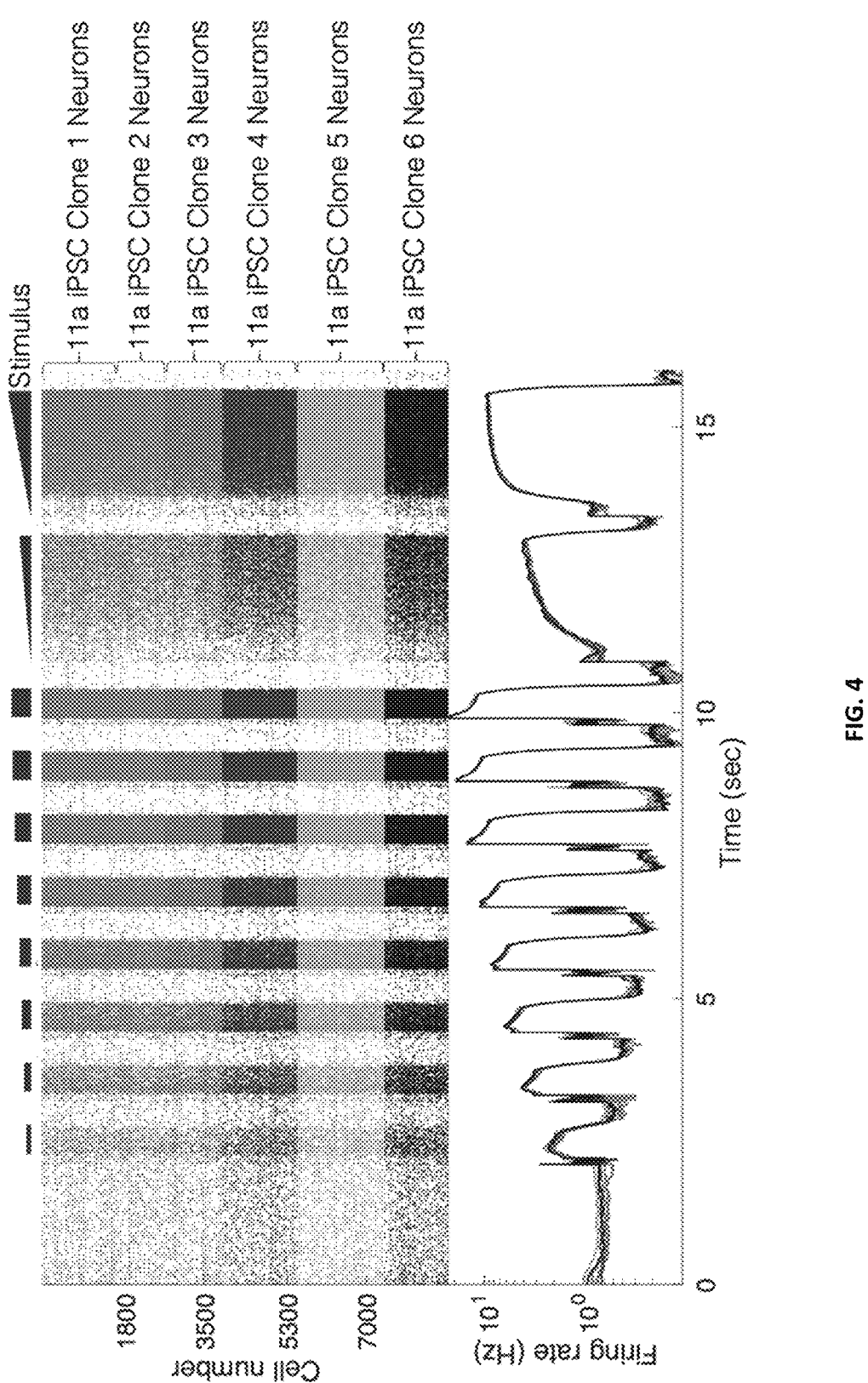
FIG. 4 describes the use of optical physiology to characterize the quality of PSC-derived neurons.

In certain aspects, the PSC-derived neurons are transformed with an optical voltage actuator and voltage reporters, the activity of which can be recorded and used to determine the functional quality of a PSC-derived neuronal reagents. FIG. 4 provides an exemplary result when PSC-derived neuronal reagents are genetically modified with optical electrophysiology constructs which allows the functional characterization and QC of the neuronal preparation. FIG. 4 shows that when neuronal preparations from 6 different clones of the same genetic background PSC cell line (11a) are characterized using all optical electrophysiology (Optopatch), thousands of individuals neurons fire multiple action potentials, suggesting mature functional properties.

FIG. 4. also shows that the average functional behavior of the 6 different neuronal preparations is strikingly similar, demonstrating high-quality of the neuronal reagents produced with the methods described in the present invention.

As shown, FIG. 4 provides optical physiology characterization of human iPS cell-derived neurons obtained by overexpression of transcription factor NGN2 in 11a iPS cell clones. Briefly, neurons were cultured for 30 days and genetically modified with all optical electrophysiology constructs to allow for stimulation (via blue light) of activity. The figure shows a Raster Plot, in which each row represents a single neuron measured and each dot represents a single action potential for that neuron in the course of the of ~15 second experiment. >1,500 neurons were recorded from neuronal cultures obtained from 6 different clones of the same iPS cell genetic background (11a) for a total of ~10,000 neurons. The average functional behavior (firing rate) for the 6 different neuronal preparations is strikingly similar, demonstrating high-quality of the neuronal reagents produced with the methods described in the present invention.

The genetically encoded reporter, actuator, or both may be delivered by any suitable expression vector using methods known in the art. An expression vector is a specialized vector that contains the necessary regulatory regions needed for expression of a gene of interest in a host cell. In some embodiments the gene of interest is operably linked to another sequence in the vector. In certain aspects, it is preferred that the viral vectors are replication defective, which can be achieved for example by removing all viral nucleic acids that encode for replication. A replication defective viral vector will still retain its infective properties and enters the cells in a similar manner as a replicating vector, however once admitted to the cell a replication defective viral vector does not reproduce or multiply. The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

Many viral vectors or virus-associated vectors are known in the art. Such vectors can be used as carriers of a nucleic acid construct into the cell. Constructs may be integrated and packaged into non-replicating, defective viral genomes like Adenovirus, Adeno-associated virus (AAV), or Herpes simplex virus (HSV) or others, including retroviral and lentiviral vectors, for infection or transduction into cells. The vector may or may not be incorporated into the cell's genome. The constructs may include viral sequences for transfection, if desired. Alternatively, the construct may be incorporated into vectors capable of episomal replication, such as an Epstein Barr virus (EPV or EBV) vector. The inserted material of the vectors described herein may be operatively linked to an expression control sequence when the expression control sequence controls and regulates the transcription and translation of that polynucleotide sequence. In some examples, transcription of an inserted material is under the control of a promoter sequence (or other transcriptional regulatory sequence) which controls the expression of the recombinant gene.

In certain aspects, a recombinant cell containing an inducible promoter is used and exposed to a regulatory agent or stimulus by externally applying the agent or stimulus to the cell or organism by exposure to the appropriate environmental condition or the operative pathogen. Inducible promoters initiate transcription only in the presence of a regulatory agent or stimulus. Examples of inducible promoters include the tetracycline response element and promoters derived from the beta-interferon gene, heat shock gene, metallothionein gene or any obtainable from steroid hormone-responsive genes. Inducible promoters which may be used in performing the methods of the present invention include those regulated by hormones and hormone analogs such as progesterone, ecdysone and glucocorticoids as well as promoters which are regulated by tetracycline, heat shock, heavy metal ions, interferon, and lactose operon activating compounds. See Gingrich and Roder, 1998, Inducible gene expression in the nervous system of transgenic mice, Annu Rev Neurosci 21:377-405. Tissue specific expression has been well characterized in the field of gene expression and tissue specific and inducible promoters are well known in the art. These promoters are used to regulate the expression of the foreign gene after it has been introduced into the target cell. In certain aspects, a cell-type specific promoter or a tissue-specific promoter is used. A cell-type specific promoter may include a leaky cell-type specific promoter, which regulates expression of a selected nucleic acid primarily in one cell type, but cause expression in other cells as well. For expression of an exogenous gene specifically in neuronal cells, a neuron-specific enolase promoter can be used. See Forss-Petter et al., 1990, Transgenic mice expressing beta-galactosidase in mature neurons under neuron specific enolase promoter control, Neuron 5: 187-197. For expression of an exogenous gene in dopaminergic neurons, a tyrosine hydroxylase promoter can be used.

In certain aspects, the expression vector is a lentiviral vector. Lentiviral vectors may include a eukaryotic promoter. The promoter can be any inducible promoter, including synthetic promoters, that function as promoters in a eukaryotic cell. For example, the eukaryotic promoter can be, but is not limited to, CamKIIα promoter, human Synapsin promoter, ecdysone inducible promoters, E1a inducible promoters, tetracycline inducible promoters etc., as are well known in the art. In addition, the lentiviral vectors used herein can further comprise a selectable marker, which can comprise a promoter and a coding sequence for a selectable trait. Nucleotide sequences encoding selectable markers are well known in the art, and include those that encode gene products conferring resistance to antibiotics or anti-metabolites, or that supply an auxotrophic requirement. Examples of such sequences include, but are not limited to, those that encode thymidine kinase activity, or resistance to methotrexate, ampicillin, kanamycin, among others. Use of lentiviral vectors is discussed in Wardill et al., 2013, A neuron-based screening platform for optimizing genetically-encoded calcium indicators, PLoS One 8(10):e77728; Dottori, et al., Neural development in human embryonic stem cells-applications of lentiviral vectors, J Cell Biochem 112(8):1955-62; and Diester et al., 2011, An optogenetic toolbox designed for primates, Nat Neurosci 14(3):387-97. When expressed under a CaMKIIα promoter in cultured rat hippocampal neurons the Optopatch construct exhibits high expression and good membrane trafficking of both CheRiff and QuasAr2.

In some embodiments the viral vector is an adeno-associated virus (AAV) vector. AAV can infect both dividing and non-dividing cells and may incorporate its genome into that of the host cell. One suitable viral vector uses recombinant adeno-associated virus (rAAV), which is widely used for gene delivery in the CNS.

In certain aspects, methods of the invention use a Cre-dependent expression system. Cre-dependent expression includes Cre-Lox recombination, a site-specific recombinase technology that uses the enzyme Cre recombinase, which recombines a pair of short target sequences called the Lox sequences. This system can be implemented without inserting any extra supporting proteins or sequences. The Cre enzyme and the original Lox site called the LoxP sequence are derived from bacteriophage P1. Bacteriophage P1 uses Cre-lox recombination to circularize and replicate its genomic DNA. This recombination strategy is employed in Cre-Lox technology for genome manipulation, which requires only the Cre recombinase and LoxP sites. Sauer &

Henderson, 1988, Site-specific DNA recombination in mammalian cells by the Cre recombinase of bacteriophage P1, PNAS 85:5166-70 and Sternberg & Hamilton, 1981, Bacteriophage P1 site-specific recombination. I. Recombination between LoxP sites, J Mol Biol 150:467-86. Methods may use a Cre recombinase-dependent viral vector for targeting tools such as channelrhodopsin-2 (ChR2) to specific neurons with expression levels sufficient to permit reliable photostimulation. Optogenetic tools such as ChR2 tagged with a fluorescent protein such as mCherry (e.g., ChR2mCherry) or any other of the tools discussed herein are thus delivered to the cell or cells for use in characterizing those cells.

The delivery vector may include Cre and Lox. The vector may further optionally include a Lox-stop-Lox (LSL) cassette to prevent expression of the transgene in the absence of Cre-mediated recombination. In the presence of Cre recombinase, the LoxP sites recombine, and a removable transcription termination Stop element is deleted. Removal of the stop element may be achieved through the use of AdenoCre, which allows control of the timing and location of expression. Use of the LSL cassette is discussed in Jackson, et al., 2001, Analysis of lung tumor initiation and progression using conditional expression of oncogenic K-ras, Genes & Dev 15:3243-3248.

In certain aspects, a construct of the invention uses a "flip-excision" switch, or FLEX switch (FLip EXicision), to achieve stable transgene inversion. The FLEX switch is discussed in Schnutgen et al., 2003, A directional strategy for monitoring Cre-mediated recombination at the cellular level in the mouse, Nat Biotechnol 21:562-565. The FLEX switch uses two pairs of heterotypic, antiparallel LoxP-type recombination sites which first undergo an inversion of the coding sequence followed by excision of two sites, leading to one of each orthogonal recombination site oppositely oriented and incapable of further recombination. A FLEX switch provides high efficiency and irreversibility. Thus in some embodiments, methods use a viral vector comprising rAAV-FLEX-rev-ChR2mCherry. Additionally or alternatively, a vector may include FLEX and any other optogenetic tool discussed herein (e.g., rAAV-FLEX-QuasAr, rAAV-FLEX-CheRiff). Using rAAV-FLEX-rev-ChR2mCherry as an illustrative example, Cre-mediated inversion of the ChR2mCherry coding sequence results in the coding sequence being in the wrong orientation (i.e., rev-ChR2mCherry) for transcription until Cre inverts the sequence, turning on transcription of ChR2mCherry. FLEX switch vectors are discussed in Atasoy et al., 2009, A FLEX switch targets channelrhodopsin-2 to multiple cell types for imaging and long-range circuit mapping, J Neurosci 28(28): 7025-7030.

Use of a viral vector such as Cre-Lox system with an optical reporter, optical actuator, or both (optionally with a FLEX switch and/or a Lox-Stop-Lox cassette) for labeling and stimulation of neurons allows for efficient photo-stimulation with only brief exposure (1 ms) to less than 100 μW focused laser light or to light from an optical fiber. Such Further discussion may be found in Yizhar et al., 2011, Optogenetics in neural systems, Neuron 71(1):9-34; Cardin et al., 2010, Targeted optogenetic stimulation and recording of neurons in vivo using cell-type-specific expression of Channelrhodopsin-2, Nat Protoc 5(2):247-54; Rothermel et al., 2013, Transgene expression in target-defined neuron populations mediated by retrograde infection with adeno-associated viral vectors, J Neurosci 33(38):195-206; and Saunders et al., 2012, Novel recombinant adeno-associated viruses for Cre activated and inactivated transgene expression in neurons, Front Neural Circuits 6:47.

In certain aspects, actuators, reporters, or other genetic material may be delivered using chemically-modified mRNA. It may be found and exploited that certain nucleotide modifications interfere with interactions between mRNA and toll-like receptor, retinoid-inducible gene, or both. Exposure to mRNAs coding for the desired product may lead to a desired level of expression of the product in the cells. See, e.g., Kormann et al., 2011, Expression of therapeutic proteins after delivery of chemically modified mRNA in mice, Nat Biotech 29(2):154-7; Zangi et al., 2013, Modified mRNA directs the fate of heart progenitor cells and induces vascular regeneration after myocardial infarction, Nat Biotech 31:898-907.

It may be beneficial to culture or mature the neurons after transformation with the genetically encoded optical reporter with optional actuator. The neurons are matured for 8-10 days post infection. In certain aspects, a prolonged culture of 30-60 days is used. Using microscopy and analytical methods described herein, the cell and its action potentials may be observed. For additional discussion, see U.S. Pub. 2013/0224756, incorporated by reference in its entirety for all purposes.

In certain aspects, the PSC-derived neural cells can be assayed using a multi-well plate microscope that illuminates a sample with near-TIR light in a configuration that allows living cells to be observed and imaged within wells of a plate. The microscope illuminates the sample from the side rather than through the objective lens, which allows more intense illumination, and a corresponding lower numerical aperture and larger field of view. By using illumination light at a wavelength distinct from the wavelength of fluorescence, the TIR microscope allows the illumination wavelengths to be nearly completely removed from the image with optical filters, resulting in images that have a dark background with bright areas of interest. The microscope can observe fluorescence to provide indicative measures of cellular action potentials from which action potential features/parameters are extracted.

Fluorescent reporters of membrane action potential, such as QuasAr2 and QuasAr3, require intense excitation light in order to fluoresce. Low quantum efficiency and rapid dynamics demand intense light to measure electrical potentials. The illumination subsystem is therefore configured to emit light at high wattage or high intensity. Characteristics of a fluorophore such as quantum efficiency and peak excitation wavelength change in response to their environment. The intense illumination allows that to be detected. Autofluorescence caused by the intense light is minimized by the microscope in multiple ways. The use of near-TIR illumination exposes only a bottom portion of each well to the illumination light, thereby reducing excitation of the culture medium or other components of the device. Additionally, the microscope is configured to provide illumination light that is distinct from imaging light. Optical filters in the imaging subsystem filter out illumination light, removing unwanted fluorescence from the image. Cyclic olefin copolymer (COC) dishes for culturing cells enable reduced background autofluorescence compared to glass. The prism is coupled to the multi-well plate through an index-matching low-autofluorescence oil. The prism is also composed of low autofluorescence fused silica.

The microscope is configured to optically characterize the dynamic properties of cells. The microscope realizes the full potential of all-optical characterization by simultaneously achieving: (1) a large field of view (FOV) to allow measurement of interactions between cells in a network or to measure many cells concurrently for high throughput; (2)

high spatial resolution to detect the morphologies of individual cells in wells and facilitate selectivity in signal processing; (3) high temporal resolution to distinguish individual action potentials; and (4) a high signal-to-noise ratio to facilitate accurate data analysis. The microscope can provide a field of view sufficient to capture tens or hundreds of cells. The microscope and associated computer system provide an image acquisition rate on the order of at least 1 kilohertz, which corresponds to a very short exposure time on the order of 1 millisecond, thereby making it possible to record the rapid changes that occur in electrically active cells such as neurons. The microscope can therefore acquire fluorescent images using the recited optics over a substantially shorter time period than prior art microscopes.

The microscope achieves all of those demanding requirements to facilitate optically characterizing the dynamic properties of cells. The microscope provides a large FOV with sufficient resolution and light gathering capacity with a low numerical aperture (NA) objective lens. The microscope can image with magnification in the range of 2× to 6× with high-speed detectors such as sCMOS cameras. To achieve fast imaging rates, the microscope uses extremely intense illumination, typically with fluence greater than, e.g., 50 $W/cm^2$ at a wavelength of about 635 nm up to about 2,000 $W/cm^2$.

Despite the high-power levels, the microscope nevertheless avoids exciting nonspecific background fluorescence in the sample, the cell growth medium, the index matching fluid, and the sample container. Near-TIR illumination limits the autofluorescence of unwanted areas of the sample and sample medium. Optical filters in the imaging subsystem prevent unwanted light from reaching the image sensor. Additionally, the microscope prevents unwanted autofluorescence of the glass elements in the objective lens by illuminating the sample from the side, rather than passing the illumination light through the objective unit. The objective lens of the microscope may be physically large, having a front aperture of at least 50 mm and a length of at least 100 mm, and containing numerous glass elements.

Preparing plates of PSC-derived neurons for imaging using the microscope may include using, for example, MatTek dishes (MatTek corp.; 10 mm glass diameter, #1.5) coated with 10 µg/mL fibronectin (Sigma-Aldrich) in 0.1% gelatin overnight at 4° C. Trypsinized CaViar and CheRiff-expressing cells are first mixed at a ratio of 5:1 CaViar:CheRiff, and then pelleted. The combined cells are re-suspended in 2.1 mL of maintenance medium and plated at a density of 2.5×104 cells/cm2 in 100 µL of plating medium to cover the entire glass surface. Cells are kept at 37° C. in 5% CO2 overnight to adhere to the glass. Maintenance medium (1.0 mL) is added to each dish and the cells are fed every 48 hours by removing 750 µL of medium from the dish and replacing with 750 µL fresh maintenance medium. The medium can be supplemented with laminin, and every medium replacement provides a decreased concentration.

For simultaneous voltage and calcium imaging, MatTek dishes (10 mm glass diameter) can be prepared to segregate CheRiff-expressing cells from CaViar-expressing cells. This allows simultaneous calcium imaging and CheRiff stimulus, both with blue light, without optical crosstalk between the two functions. In certain aspects, 8 mm-diameter polydimethylsiloxane (PDMS) discs are treated with a solution of 10 µg/mL fibronectin in 0.1% gelatin on one side for 10 minutes at room temperature. The coated discs are then dried and then pressed onto the MatTek dish glass surface, slightly offset to one side. The remaining exposed area of the glass is then coated with 10 µg/mL fibronectin in 0.1% gelatin.

Cells expressing the CheRiff are trypsinized according to the manufacturer's protocol and re-suspended in 50 µL of maintenance medium per dish. For plating, 50 µL of the CheRiff cells are then added to the exposed portion of the glass surface and allowed to sit for 40 minutes at 37° C. in 5% CO2 to allow the cells to adhere. The PDMS discs are then removed, the glass surface washed with 150 µL of maintenance medium and the remaining volume aspirated. Trypsinized CaViar cells are then re-suspended in 100 µL of maintenance medium per dish and plated at a density of 2.0×104 cells/cm2 in 100 µL to cover the entire glass surface. Cells are kept at 37° C. in 5% CO2 overnight to adhere to the glass. 1.0 0 mL of maintenance medium is added to each dish and the cells were fed every 48 hours by removing 750 µL of medium from the dish and adding 750 µL fresh maintenance medium.

In certain aspects, neurons and methods of the invention may be used to create disease models for in vitro investigation of disease. Neurons may be derived from iPSCs taken from individuals suffering from the neuronal disease or may be derived through genome editing by incorporating genotype associated with the neuronal disease. In certain instances, a test mutation, suspected of being associated with a neuronal disease, may be incorporated into a neuron through genome editing and the resulting modified neuron may be observed for signs of disease to evaluate the test mutation for links to the disease.

Figure 5:
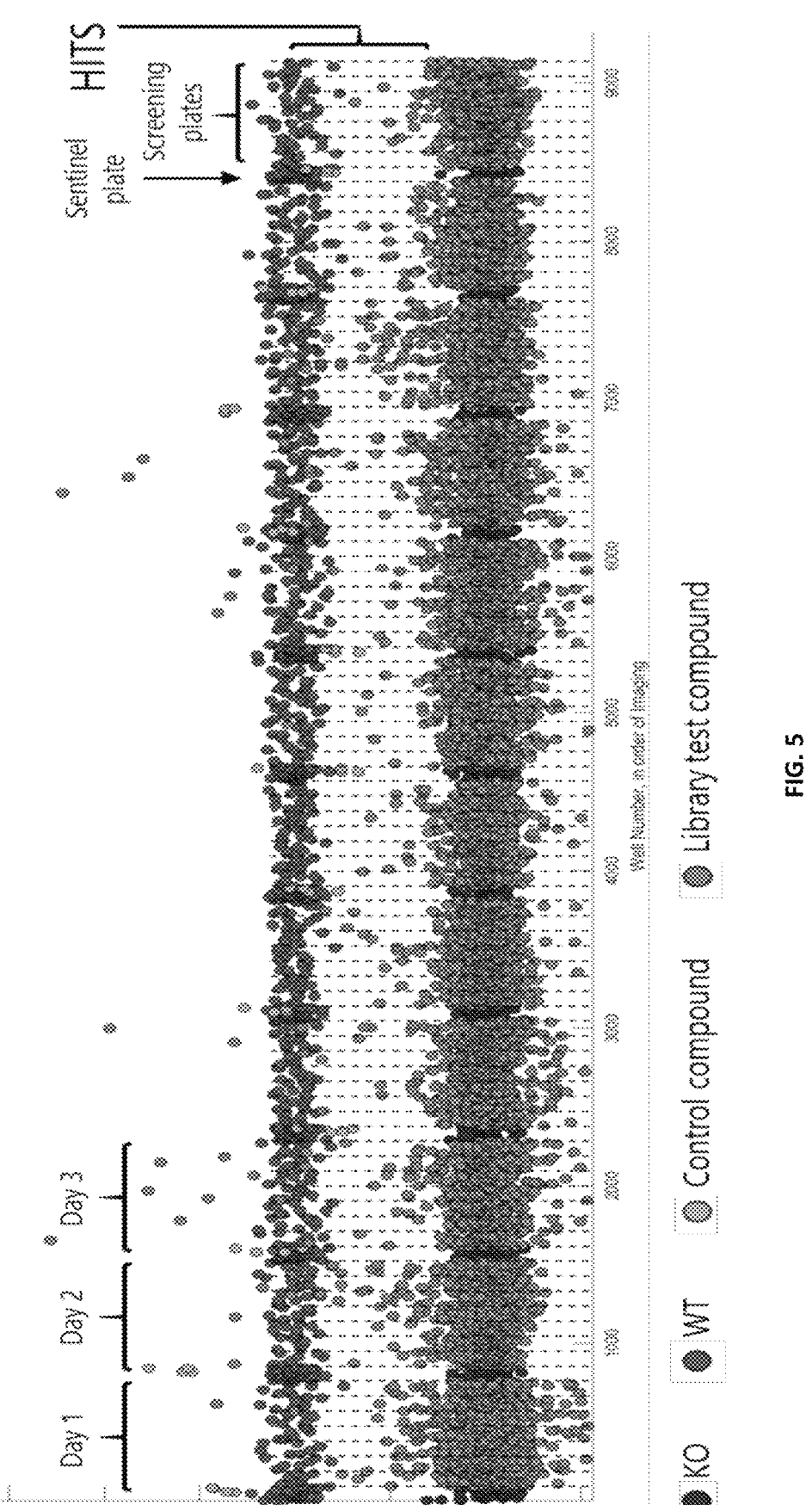
FIG. 5 provides an example of the utility of PSC-derived neurons in a high throughput phenotypic screen using reagents from a single cryopreserved lot of about 7 billion neurons.

In certain aspects, the PSC-derived neuronal cells representing a disease model and genetically modified to express optical reporters can be used in a multi-well plate fluorescence microscope to screen for small molecule compounds that can revert the disease phenotype to a control state (phenotype of healthy PSC-neurons without mutations). FIG. 5 provides an example of the utility of PSC-derived neurons in a high throughput phenotypic screen using reagents from a single cryopreserved lot of ~7 billion neurons.

Briefly, FIG. 5 shows phenotypic screening in human iPS cell-derived neurons. The figure shows representative data from 12 days of a phenotypic screen in loss-of-function (knockout or KO) model for a monogenetic form of Epilepsy. Control Wildtype ("WT") and Disease "KO" human iPS cell-derived cortical excitatory neurons were produced and frozen at large scale (total of ~7 billion neurons) using the methods described in the present invention. A small subset of the neuronal reagents was thawed with high viability, plated and culture for 30 days onto 96-well plates. Neurons were modified with genetic constructs expressing Optical reporters to allow for measurements of electrophysiological activity. Functional comparisons between the WT and KO neurons established a multidimensional phenotype which is quantified by a disease score, a linear combination of many parameters. The present inventors have executed a 30,000-compound screen for molecules that reverse the phenotype; results from the first 9,000 wells are shown and have a ~1.5% hit rate at a disease score threshold of 0.5. The results reveal a consistent phenotype and a stable assay (mean Z'=0.4). Each dashed line corresponds to one 96-well plate.

In certain aspects, for example where modelled disease are non-monogenic, complex etiology and/or late onset, neurons of the invention may be cultured for extended periods, such as 1 month, 2 months, 3 months, 4 months or longer in order to simulate aging. See Sanchez-Danes, et al. Cells of the invention may be transformed with optical reporters of membrane potential, reporters of intracellular calcium levels, light-gated ion channels, or a combination thereof. Cells may be monitored over time by inducing and observing action potentials and changes in intracellular calcium levels during disease progression in order to examine the neuronal effects of the disease. Subject cells of the disease model may also be monitored pre and post application of various therapies in order to evaluate their effectiveness.

Cells and methods of the invention may include the use of tool/test compounds or other interventional tools applied to the observed cell or cells. Application of test compounds can reveal effects of those compounds on cellular electrophysiology. Use of a tool compounds can achieve greater specificity in diagnosis or for determining disease mechanisms, e.g. by blocking certain ion channels. By quantifying the impact of the compound, one can quantify the level of that channel in the cell.

With a tool or test compound, a cell may be caused to express an optical reporter of neural or electrical activity and may also be exposed to a compound such as a drug. A signature of the cell can be observed before, during, or after testing the compound. Any combination of different cells and cell types can be exposed to one or any combination of compounds, including different test compound controls. Multi-well plates, multi-locus spotting on slides, or other multi-compartment lab tools can be used to cross-test any combination of compounds and cell types.

In certain aspects, tool compounds are added to cells and their effect on the cells is observed to distinguish possible diseases or causes or mechanisms of diseases. For example, where two or more cells in synaptic connection with one another are observed, extrinsic stimulation of an upstream cell should manifest as an action potential in a downstream cell. A compound that is known to inhibit neurotransmitter reuptake may be revealed to work on only certain neural subtypes thus indicating a specific disease pattern.

In certain aspects, the PSC-derived neural cells are assayed to detect, measure, or evaluate synaptic transmission. A signature may be observed for a cell other than the cell to which direct stimulation was applied. In fact, using the signal processing algorithms discussed herein, synaptic transmission among a plurality of cells may be detected thus revealing patterns of neural connection. Establishing an assay that successfully detects firing of a downstream neuron upon stimulation of an upstream neuron can reveal, where the subject cell to be observed fails to fire upon stimulation of an upstream neuron, a disease or condition characterized by a failure of synaptic transmission.

Test compounds can be evaluated as candidate therapies to determine suitability of a treatment prior to application to patient. E.g. one can test Alzheimer's disease drugs to find the one that reverts the firing pattern back to wild-type, prevents or delays disease onset, or lessens disease symptoms.

In certain aspects, the PSC-derived neural cells can be used in systems and methods to identify possible therapies for a patient by testing compounds, which systems and methods may be employed as personalized medicine. Due to the nature of the assays described herein, it may be possible to evaluate the effects of candidate therapeutic compounds on a per-patient basis thus providing a tool for truly personalized medicine. For example, an assay as described herein may reveal that a patient suffering from a certain disease has neurons or neural subtypes that exhibit a disease-type physiological phenotype under the assays described herein. One or a number of different compounds may be applied to those neurons or neural subtypes. Cells that are exposed to one of those different compounds (or a combination of compounds)

may exhibit a change in physiological phenotype from disease-type to normal. The compound or combination of compounds that affects the change in phenotype from disease-type to normal is thus identified as a candidate treatment compound for that patient.

In certain aspects, test compounds may include A2A receptor antagonists, levodopa, amantadine, dopamine agonists, selective MAO-B inhibitors, anticholinergic drugs, or catechol O-methyltransferase (COMT) inhibitors.

EXAMPLES

Example 1

Control iPS cell lines are maintained in culture using mTeSR1™ medium (STEMCELL Technologies™) and Matrigel™ (Corning) coating according to manufacturers' protocols. The iPS cell lines are differentiated into Ngn2 excitatory neurons using a transcriptional programming approach, whereby iPS cell lines are initially modified via lentiviral delivery of a construct expressing the reverse tetracycline transactivator (rtTA) and a tetracycline-responsive (TetOp) construct driving the expression of the proneuronal transcription factor NGN2 and a puromycin resistant enzyme.

Figure 3:
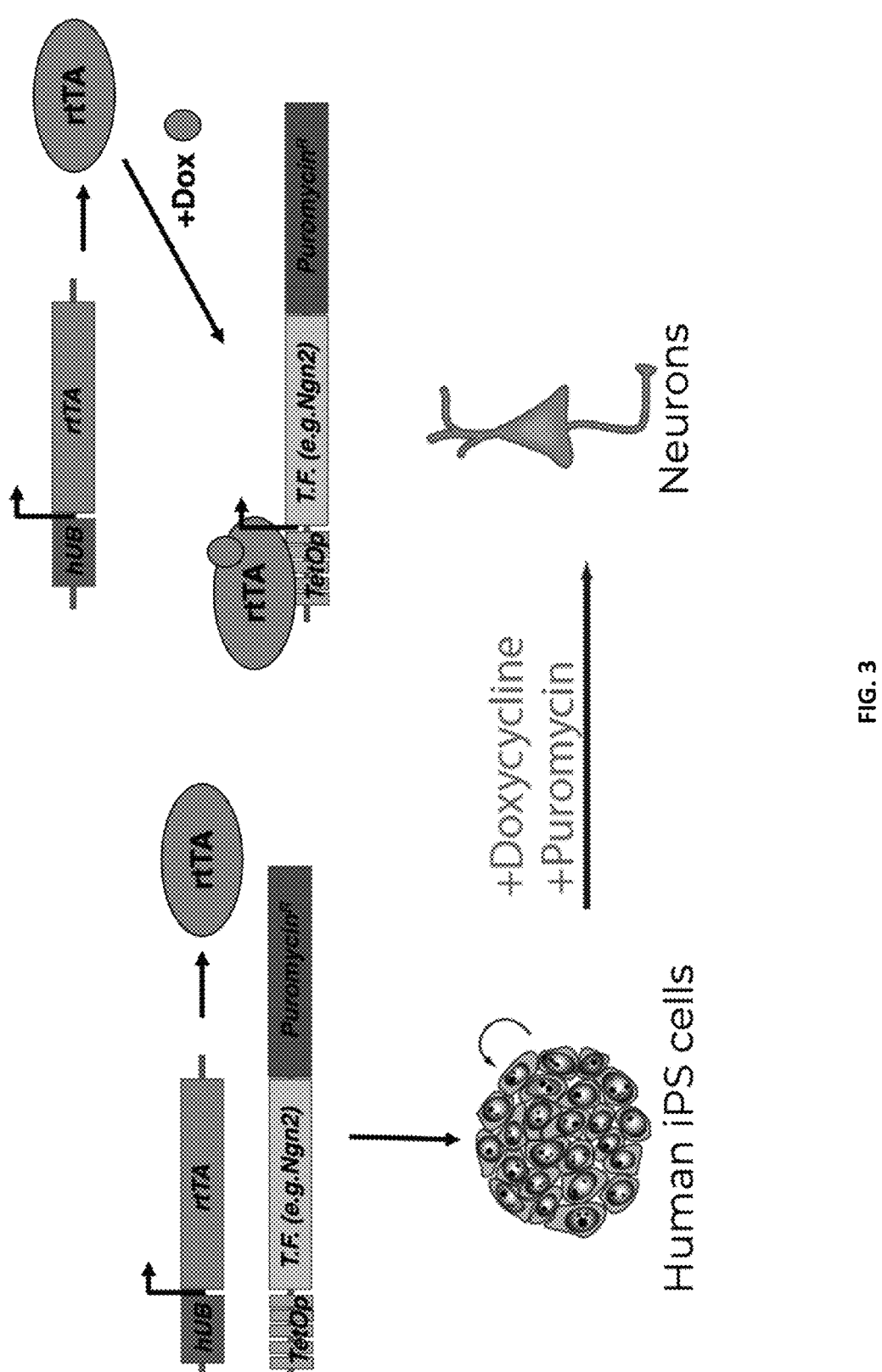
FIG. 3 provides a schematic of an inducible construct.

FIG. 3 provides schematics of exemplary inducible expression constructs used to genetically modify human iPS cells for neuronal conversion. Two constructs are used. One construct expresses from a constitutive promoter (e.g. Ubiquitin Promoter: UB) the reverse tetracycline trans-activator (rtTA). The other construct expresses a transcription factor (T.F.) for instance Neurogenin-2 (Ngn2) translationally fused to an antibiotic resistance gene (e.g. Puromycin), driven by Tetracycline-responsive regulatory elements (TetOp). Both constructs are introduced into human iPS cells via lentiviral transduction. Genetically modified iPS cells can be expanded to increase starting material for large scale production. In the presence of doxycycline (Dox), rtTA protein binds and activates the TetOp to drive high level expression of the transcription factor and antibiotic resistance gene. After 3-5 days of doxycycline and antibiotic treatment a homogenous preparation of immature neurons can be obtained.

Genetically modified iPS cell lines are expanded in mTeSR1™ medium for 3-5 passages prior to induction of NGN2. For neuronal production, iPS cells are dissociated with Accutase™ according to manufacturer's recommendations and plated at a density of 300,000 cells/cm$^2$ using mTeSR1™ medium supplemented with 10 μM Rock Inhibitor (Sigma) and 2 μg/mL doxycycline (Sigma) to initiate NGN2 overexpression. Differentiating cells are subsequently maintained for 3 days in 1:1 DMEM/F12: Neurobasal Medium (ThermoFisher Scientific) supplemented with 1×GlutaMAX, 1×non-essential amino acids, 1×N2 (Gibco), 1×B-27, 2 μg/mL doxycycline (Sigma) and 2 μg/mL puromycin. This process results in a pure population of neurons that were dissociated with Accutase™.

The neurons are cryopreserved and subsequently thawed and plated at 80,000 cells/cm$^2$ onto poly-d-lysine/laminin pre-coated single-well (MatTek™) or 8-well (Ibidi) dishes for prolonged culture. Neuronal cultures are maintained until DIV18 in Neurobasal A Medium supplemented with 1×GlutaMAX, 1×nonessential amino acids, 1×N2 (Gibco), 1×B-27, 10 ng/mL BDNF (R&D) and 10 ng/mL GDNF (R&D). Three days after plating, neuronal cultures are supplemented with 40,000 cells/cm$^2$ of primary mouse glial cells.

Lentiviral particles encoding Optopatch components CheRiff and QuasAr are produced. Neuronal cultures are transduced on DIV10 with CheRiff-mOrange2 and QuasAr3Citrine constructs driven by the CAMK2A promoter to target expression of the Optopatch components to mature excitatory neurons. QuasAr3-Citrine is a variant of QuasAr2 which incorporates multiple $K_{ir}2.1$ trafficking sequences and a lysine (putative ubiquitination site) to arginine substitution at position 171, resulting in improved expression and trafficking. Transduction of neuronal cultures is carried out, with washing of the virus by 2× medium exchanges 16-24 h after treatment (DIV11). Neuronal cultures are maintained until DIV25, when neurons were recorded using Optopatch imaging.

One week prior to Optopatch measurements, neuronal cultures are switched to BrainPhys™ Neuronal medium (STEMCELL Technologies) supplemented with 1×N2–A, 1×SM1 (STEMCELL Technologies), 10 ng/mL BDNF (R&D) and 10 ng/mL GDNF (R&D).

Accordingly, the present invention provide methods by which PSCs are differentiated into neural cells, cryopreserved, cultured, transduced with optogenetic proteins, and assayed using an optogenetic assay.

Example 2

To characterize the intrinsic excitability activity of human iPS cell-derived excitatory neurons with the Optopatch platform the two iPS cell lines, "11a" and "20b", from Example 1 were used. These two iPS cell lines were derived from two neurologically healthy male subjects. The 11a and 20b iPS cells are converted into excitatory neurons using a transcriptional programming approach whereby the pro-neuronal transcription factor NEUROGENIN2 (NGN2) is overexpressed using doxycycline responsive lentiviral constructs as described in Example 1. This process drives the rapid conversion of iPS cells into neurons that resemble cortical excitatory neurons.

The resulting neurons are cryopreserved and subsequently thawed.

The thawed cells are co-cultured with primary rodent glia to facilitate neuronal electrophysiological maturation. To enable Optopatch measurements, the cells are transduced with lentiviral constructs expressing Optopatch components driven by the neuronal excitatory promoter CAMK2A and signals are recorded from the cells 2 weeks later. At the time of Optopatch measurements, the NGN2 excitatory neuron are homogeneous and electrophysiologically active, yielding highly stereotyped and reproducible data across cells, dishes, differentiation rounds and cell lines.

To confirm effective conversion of iPS cells from both genetic backgrounds into excitatory neurons, neuronal preparations are used at the time of electrophysiological measurements (DIV25-DIV30).

To determine neuronal production efficiency, cultures are immunostained using antibodies against a human-specific nuclear antigen (hNuclei) and the mature pan-neuronal cytoskeletal protein microtubule-associated protein 2 (MAP2). The percentage of human differentiated cells in the cultures is estimated and correlated to neurons by calculating percentage of MAP2+cells over hNuclei+cells. Large nuclei not stained with the hNuclei immunoreagent correspond to nuclei of murine glial cells used as a supportive monolayer. Greater than 94% of human differentiated cells express the MAP2 protein, which shows the expected localization in proximal neurites, indicating successful neuronal production.

An antibody against the inhibitory neurotransmitter GABA is used to determine the fraction of GABAergic neurons in the cultures at the time of Optopatch measurements. Consistent with previous studies reporting enrichment for excitatory neurons when using an Ngn2-mediated programming approach less than <4% of human differentiated neurons (MAP2+cells) in the Ngn2 neuronal/mouse glia co-cultures show strong immunoreactivity to the GABA antibody.

A qPCR-based assessment of relative transcript abundance for a subset of genes encoding potential pharmacological targets is carried out. These targets include sodium and potassium channels, and hyperpolarization-activated and cyclic nucleotide-gated (HCN) channels. A heat map of average Cq values suggests that, except for KCNJ11, KCNA1, and CHRM1 with Cq>34, most of the genes encoding the selected pharmacological targets are detected at low levels (Cq>28).

All optical measurements of electrophysiology, Optopatch, rely on the expression of the voltage actuator CheRiff, which elicits action potentials upon blue-light stimulation, and the voltage reporter QuasAr, which generates near infrared fluorescence emission as result of changes in membrane potential. Each of these two components is fused to a fluorescent protein used to monitor reporter expression levels and membrane trafficking. Robust and neuronal-specific expression of fluorescent reporters mOrange2, fused to CheRiff, and Citrine, fused to QuasAr in the neuronal preparations at the time of Optopatch characterization is observed.

Optopatch measurements are carried out in a custom-built ultra-widefield fluorescence microscope, as described herein. Using this platform, intrinsic excitability properties are recorded for 11a and 20b NGN2 neuronal cultures at DIV25 in the presence of synaptic blockers NBQX, D-AP5 and Gabazine to block AMPA, NMDA and GABA currents, respectively. A custom blue light stimulus protocol of three 500 ms blue light steps of increasing intensity (1, 15 and 75 mW/cm$^2$) followed by two 2 second ramps of linearly increasing intensity (0.5-10 mW/cm$^2$ and 0.5-110 mW/cm$^2$) is used to elicit a range of activity from individual neurons. ~50 to 100 neurons are simultaneously stimulated and recorded in a single field of view.

High signal-to-noise ratio (SNR) fluorescence-time traces are generated, and action potentials can be detected with high fidelity. Individual action potentials are detected for each of the hundreds of neurons and recorded with Optopatch and plotted on a spike raster plot, where each row represents a single neuron, and each dot represents a detected spike. While individual neurons show a diversity of spiking behavior throughout the stimulus protocol, the average firing rate of the population is remarkably similar for both cell lines.

These data demonstrate the overall consistency of neuronal production between the two cell lines in generating electrophysiologically active cells, which are cryopreserved and subsequently thawed.

The sensitivity of an excitability assay for detecting pharmacological modulation in NGN2 neurons using the well-characterized compound quinidine, which is reported to increase spike width and reduce spike activity is tested. Consistent with the anticipated effect, acute addition of quinidine to the NGN2 neurons results in dramatic changes to both the spike waveform and firing rate. These changes can be observed in the individual traces at 10 μM and 30 μM quinidine. Comparing the mean firing rate for neuronal cultures treated with different concentrations of quinidine with that of cultures treated with vehicle shows dramatic reduction in spike rate with increased blue light stimulus.

Additional quantification of both the response to quinidine and retigabine in is determined using an Optopatch excitability assay. Quinidine has been reported to block several voltage-, $Na^+$ and $Ca^{++}$ gated potassium channels ($K_{Na}1.1$, $K_{Ca}5.1$, $K_{2P}16.1$, $K_v1.5$, $K_v1.7$, $K_v10.1$, $K_v10.2$), including two-pore forming channels as well as voltage gated $Na^+$ channels. The KCNT1 gene encoding $K_{Na}1.1$ shows detectable expression levels in the NGN2 neurons compared to the starting iPS cell lines. The complex pharmacological activity of quinidine causes a concentration dependent broadening of the spikes.

The spike width (measured from the base of the action potential) increases, the spike rise time (measured from start to peak of the action potential) increases, the time to the maximum of the after hyperpolarization (AhP) depth increases, and the magnitude of the AhP depth (measured from the baseline fluorescence before the action potential) decreases, all at the maximum concentration tested (30 μM). At higher stimulation intensities (15 and 75 mW/cm$^2$), a concentration dependent reduction in the spike rate is also observed.

Retigabine is an activator of $K_v7.2/3/4/5$ potassium channels with efficacious concentrations in the low micromolar and nanomolar range (e.g. $K_v7.3$ $EC_{50}$ $6.31×10^{-7}$ M; $K_v7.2$ $2.5×10^{-6}$ M). Treatment of NGN2 neurons with retigabine results in a deepening of the after hyperpolarization via enhanced M-currents which act as a brake on repetitive spiking and burst generation. In line with this modulatory role of the M-currents concentration dependent reduction of the spike frequency at 15 and 75 mW/cm$^2$ stimulation intensities is observed. At the highest concentration of retigabine (30 μM) and the peak intensity (75 mW/cm$^2$), the spike frequency is reduced.

The detectable expression levels of KCNQ2 and KCNQ3 transcripts in NGN2 neurons are consistent with the strong pharmacological effect of retigabine. In total, the qPCR and Optopatch excitability assay results are consistent with the detection of pharmacological modulation from both quinidine and retigabine through ion channel targets expressed in the NGN2 neurons.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof

What is claimed is:

1. A method for producing neuronal cells, the method comprising:

obtaining pluripotent stem cells;

introducing into said cells an inducible genetic element that encodes a pro-neuronal transcription factor;

inducing expression of the genetic element in said cells, thereby causing differentiation of said cells into neuronal cells;

cryopreserving the neuronal cells;

thawing the cryopreserved neuronal cells;

maintaining the neuronal cells in in a medium supplemented with laminin at a first concentration;

replacing the medium with a second medium comprising laminin at a second concentration lower than the first concentration; and replacing the second medium with a third medium comprising laminin at a third non-zero concentration lower than the second concentration.

2. The method of claim 1, wherein the transcription factor is neurogenin-2.

3. The method of claim 1, further comprising using the neuronal cells in a biological assay.

4. The method of claim 2, wherein the thawed neuronal cells are plated and cultured in laminin coated wells of a multi-well plate.

5. The method of claim 1, further comprising transfecting the pluripotent stem cells with a plasmid encoding a nuclease and guide RNA.

6. The method of claim 5, wherein the guide RNA and nuclease are used to cause at least one knock-in or knock-out mutation.

7. The method of claim 1, wherein the pluripotent stem cells are induced pluripotent stem cells derived from cells obtained from a subject.

8. The method of claim 1, further comprising introducing one or more additional genetic constructs into the differentiated neuronal cells such that they express one or more optical reporters of cellular activity and/or optical actuators of cellular activity.

9. The method of claim 1, further comprising the step of expanding said pluripotent stem cells prior to the induction step.

10. The method of claim 1, further comprising cryopreserving and thawing the obtained pluripotent stem cells prior to the induction step.

* * * * *